United States Patent
Pic et al.

(10) Patent No.: US 12,290,250 B2
(45) Date of Patent: May 6, 2025

(54) DEVICES AND METHODS FOR DELIVERING POWDERED AGENTS

(71) Applicant: Boston Scientific Scimed, Inc., Maple Grove, MN (US)

(72) Inventors: Andrew Pic, Northboro, MA (US); Laurie Lehtinen, Boylston, MA (US); Ryan Evers, Billerica, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 808 days.

(21) Appl. No.: 17/193,598

(22) Filed: Mar. 5, 2021

(65) Prior Publication Data

US 2021/0275157 A1    Sep. 9, 2021

Related U.S. Application Data

(60) Provisional application No. 62/986,352, filed on Mar. 6, 2020.

(51) Int. Cl.
  *A61B 17/00* (2006.01)
  *A61M 11/00* (2006.01)
  *A61M 13/00* (2006.01)

(52) U.S. Cl.
  CPC ............ *A61B 17/00491* (2013.01); *A61B 2017/00367* (2013.01); *A61M 11/003* (2014.02); *A61M 13/00* (2013.01)

(58) Field of Classification Search
  CPC .... A61B 17/00491; A61B 2017/00367; A61B 2017/00292; A61B 2017/00522;
  (Continued)

(56) References Cited

U.S. PATENT DOCUMENTS

| 471,854 A | 3/1892 | Howard |
| 881,238 A | 3/1908 | Hasbrouck |

(Continued)

FOREIGN PATENT DOCUMENTS

| CN | 101401956 B | 11/2012 |
| DE | 60215438 T2 | 8/2007 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — Quynh-Nhu H. Vu
*Assistant Examiner* — Justin L Zamory
(74) *Attorney, Agent, or Firm* — Bookoff McAndrews, PLLC

(57) ABSTRACT

A device for delivering an agent may comprise: a housing defining an enclosure. The housing may be configured to store an agent. The device may further comprise an inlet, in fluid communication with the enclosure, for receiving a flow of pressurized fluid; an outlet in fluid communication with the enclosure; and a filter disposed within the enclosure. Pores of a wall of the filter may be configured such that the fluid is permitted to pass through the pores into a channel defined by an inner surface of the wall. An actuation member may be configured to transition between a first configuration, in which portions of the agent disposed proximally to the actuation member are prevented from passing distally of the actuation member, and a second configuration, in which portions of the agent disposed proximally of the actuation member are capable of passing distally of the actuation member.

19 Claims, 17 Drawing Sheets

(58) Field of Classification Search
CPC .... A61M 13/00; A61M 11/02; A61M 11/003;
A61M 2202/0028; A61M 2202/0035;
A61M 2202/0042; A61M 2202/005;
A61M 2205/75; A61M 2206/12
See application file for complete search history.

(56) References Cited

U.S. PATENT DOCUMENTS

| | | | |
|---|---|---|---|
| 1,145,520 A | 7/1915 | Smith | |
| 1,599,959 A | 9/1926 | Buheiji | |
| 1,732,566 A | 10/1929 | McKendrick | |
| 2,151,418 A | 3/1939 | Bolté | |
| 2,185,927 A | 6/1940 | Shelanski | |
| 2,478,715 A | 8/1949 | Schmitt | |
| 2,623,519 A | 12/1952 | Cohen | |
| 3,669,113 A | 6/1972 | Altounyan et al. | |
| 3,940,061 A | 2/1976 | Gimple et al. | |
| 4,184,258 A | 6/1980 | Barrington et al. | |
| 4,259,187 A * | 3/1981 | DeFrank | A61M 5/165 604/93.01 |
| 4,427,450 A | 1/1984 | Kostansek | |
| 4,457,329 A | 7/1984 | Werley et al. | |
| 4,806,167 A | 2/1989 | Raythatha | |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Kneopfler | |
| 5,312,333 A | 5/1994 | Churinetz et al. | |
| 5,366,122 A | 11/1994 | Guentert et al. | |
| 5,445,612 A | 8/1995 | Terakura et al. | |
| 5,470,311 A | 11/1995 | Setterstrom et al. | |
| 5,778,872 A * | 7/1998 | Fukunaga | A61M 16/1055 128/911 |
| 5,884,621 A | 3/1999 | Matsugi et al. | |
| 5,951,531 A | 9/1999 | Ferdman et al. | |
| 6,003,512 A | 12/1999 | Gerde | |
| 6,484,750 B1 | 11/2002 | Foos et al. | |
| 6,553,987 B1 * | 4/2003 | Davies | A61M 15/0025 128/200.14 |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 7,178,547 B2 | 2/2007 | Mackal | |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 8,673,065 B2 | 3/2014 | Burgess et al. | |
| 8,721,582 B2 | 5/2014 | Ji | |
| 8,728,032 B2 | 5/2014 | Ducharme et al. | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2 | 12/2015 | Greenhalgh et al. | |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 | 5/2017 | Pohlmann et al. | |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 | 9/2018 | Eder et al. | |
| 10,173,019 B2 | 1/2019 | Kaufmann et al. | |
| 10,384,049 B2 | 8/2019 | Stanton et al. | |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 | 5/2021 | Hernandez | |
| 2004/0107963 A1 | 6/2004 | Finlay et al. | |
| 2004/0249359 A1 | 12/2004 | Palasis et al. | |
| 2005/0121025 A1 | 6/2005 | Gamard et al. | |
| 2005/0147656 A1 | 7/2005 | McCarthy et al. | |
| 2005/0220721 A1 | 10/2005 | Kablik et al. | |
| 2006/0004314 A1 | 1/2006 | McCarthy et al. | |
| 2006/0213514 A1 | 9/2006 | Price et al. | |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0125375 A1 | 6/2007 | Finlay et al. | |
| 2007/0151560 A1 | 7/2007 | Price et al. | |
| 2007/0083137 A1 | 8/2007 | Hopman et al. | |
| 2007/0199824 A1 | 8/2007 | Hoerr et al. | |
| 2008/0021374 A1 | 1/2008 | Kawata | |
| 2008/0287907 A1 | 11/2008 | Gregory et al. | |
| 2009/0101144 A1 | 4/2009 | Gamard et al. | |
| 2009/0155342 A1 | 6/2009 | Diegemann et al. | |
| 2009/0281486 A1 | 11/2009 | Ducharme | |
| 2010/0121261 A1 | 5/2010 | Kablik et al. | |
| 2010/0305505 A1 | 12/2010 | Ducharme et al. | |
| 2011/0073200 A1 | 3/2011 | Overvaag et al. | |
| 2011/0274726 A1 | 11/2011 | Guo et al. | |
| 2011/0308516 A1 | 12/2011 | Price et al. | |
| 2014/0222067 A1 | 8/2014 | Ericson et al. | |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2016/0375202 A1 * | 12/2016 | Goodman | A61M 13/00 604/500 |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 * | 7/2018 | Smith | A61M 11/02 |
| 2018/0214160 A1 | 8/2018 | Hoskins et al. | |
| 2018/0339144 A1 | 11/2018 | Greenhalgh et al. | |

(56) References Cited

U.S. PATENT DOCUMENTS

| | | |
|---|---|---|
| 2019/0134366 A1 | 5/2019 | Erez et al. |
| 2019/0217315 A1 | 7/2019 | Maguire et al. |
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | |
|---|---|---|
| EP | 3225172 A1 | 10/2017 |
| EP | 3052168 B1 | 11/2019 |
| JP | H07118305 A | 5/1995 |
| JP | 2017176713 A | 10/2017 |
| JP | 2019092645 A | 6/2019 |
| JP | 2020503145 A | 1/2020 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2009061409 A1 | 5/2009 |
| WO | 2015050814 A1 | 4/2015 |
| WO | 2016209442 A1 | 12/2016 |
| WO | 2018157772 A1 | 9/2018 |
| WO | 2020009102 A1 | 1/2020 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, COOK, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion issued on Jun. 18, 2021 in counterpart International Patent Application No. PCT/US2021/021159 (28 pages, in English).

* cited by examiner

DEVICES AND METHODS FOR DELIVERING POWDERED AGENTS

CROSS-REFERENCE TO RELATED APPLICATIONS

This application claims the benefit of priority from U.S. Provisional Application No. 62/986,352, filed on Mar. 6, 2020, which is incorporated by reference herein in its entirety.

TECHNICAL FIELD

Various aspects of the present disclosure relate generally to devices and methods for delivering agents. More specifically, in embodiments, the present disclosure relates to devices for delivery of powdered agents, such as hemostatic agents.

BACKGROUND

In certain medical procedures, it may be necessary to minimize or stop bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may not achieve a desired rate of agent delivery or a desired dosage of agent, may result in the agent clogging portions of the delivery device, may result in inconsistent dosing of agent, or may not result in the agent reaching the treatment site deep within the GI tract. The current disclosure may solve one or more of these issues or other issues in the art.

SUMMARY

Each of the aspects disclosed herein may include one or more of the features described in connection with any of the other disclosed aspects.

A device for delivering an agent may comprise: a housing defining an enclosure. The housing may be configured to store an agent. The device may further comprise an inlet, in fluid communication with the enclosure, for receiving a flow of pressurized fluid; an outlet in fluid communication with the enclosure; and a filter disposed within the enclosure. A wall of the filter may include a plurality of pores. The pores may be configured such that the fluid is permitted to pass through the pores into a channel defined by an inner surface of the wall. The device may further comprise an actuation member disposed within the enclosure. The actuation member may be configured to transition between a first configuration, in which portions of the agent disposed proximally to the actuation member are prevented from passing distally of the actuation member, and a second configuration, in which portions of the agent disposed proximally of the actuation member are capable of passing distally of the actuation member.

Any of the devices disclosed herein may have any of the following features. The actuation member may include a rotatable shaft. The rotatable shaft may include an opening extending substantially perpendicularly to a longitudinal axis of the rotatable shaft. In the second configuration, the agent may be capable of passing through the opening. The opening may include a first portion, in which a diameter of the opening tapers radially inward, in a distal direction, relative to a longitudinal axis of the opening, and a second portion, in which the diameter of the opening is constant. The opening may include a third portion, distal to the second portion, in which the diameter of the opening tapers radially outward, in a distal direction, relative to the longitudinal axis of the opening. The channel may include a first portion, in which a diameter of the channel tapers radially inward, in a distal direction, relative to a longitudinal axis of the channel. The first portion may terminate distally in a distal end. The channel may include a second portion, adjacent to the distal end, in which the diameter is constant. The second portion of the channel may be proximal of the first portion of the opening. The channel may include a third portion, distal to the opening. In the third portion of the channel, the diameter of the channel may taper radially inward, in the distal direction, relative to the longitudinal axis of the channel. The filter may be sintered. The pores may extend along tortuous paths. The pores may be configured such that the agent is not permitted to pass through the pores. The agent may be a powder having a particle diameter between 50 microns and 600 microns. The pores may have a diameter between 2 microns and 100 microns. The fluid may be permitted to pass through the outlet in both the first configuration and the second configuration. The actuation member may be a slider configured to move in a plane substantially perpendicular to a longitudinal axis of the housing. The fluid may exit the filter in a turbulent flow pattern.

In another example, a device for delivering an agent may comprise: a housing defining an enclosure. The housing may be configured to store an agent. An inlet may be in fluid communication with the enclosure, for receiving a flow of pressurized fluid. A filter may be disposed within the enclosure. A wall of the filter may include a plurality of pores. The pores may be configured such that the flow of fluid is permitted to pass through the pores into a channel defined by an inner surface of the wall. The pores may be configured such that the agent is not permitted to pass through the pores. An outlet may be fluid communication with the channel. An actuation member may be disposed within the enclosure. The actuation member may be configured to transition between a first configuration, in which the agent is not permitted to pass through the outlet, and a second configuration, in which the agent is permitted to pass through the outlet. The fluid may be permitted to pass through the outlet in both the first configuration and the second configuration.

Any of the devices disclosed herein may have any of the following features. Fluid from the fluid inlet may only be permitted to pass through the outlet after passing through the pores. The actuation member may include a rotatable shaft having an opening extending substantially perpendicularly to a longitudinal axis of the rotatable shaft, and wherein, in the second configuration, the agent is permitted to pass through the opening.

In another example, a device for delivering an agent may comprise: a housing defining an enclosure and configured to hold a powder. The powder may have a particle dimension between 50 microns and 600 microns. An inlet may be in fluid communication with the enclosure for receiving a flow of pressurized gas. A sintered filter may be disposed within the enclosure. A wall of the filter may include a plurality of tortuously-extending pores. The pores may be configured such that the gas is permitted to pass through the pores into a channel defined by a surface of the wall. The pores may be configured such that the powder is not permitted to pass through the pores. The pores may have a diameter between 2 microns and 100 microns. An outlet may be in fluid communication with the channel. An actuation member may be disposed within the enclosure. The actuation member may be configured to transition between a first configuration, in which a combination of the gas and the powder are permitted to pass through the outlet, and a second configuration, in which only the gas is permitted to pass through the outlet.

Any of the devices described herein may have any of the following features. The actuation member may include a rotatable shaft having an opening extending substantially perpendicularly to a longitudinal axis of the rotatable shaft. In the second configuration, the agent may be permitted to pass through the opening.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "distal" refers to a direction away from an operator, and the term "proximal" refers to a direction toward an operator. The term "exemplary" is used in the sense of "example," rather than "ideal." The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate aspects of the present disclosure and together with the description, serve to explain the principles of the disclosure.

DETAILED DESCRIPTION

Embodiments of this disclosure relate to enclosures for storing an agent (e.g., a powdered agent) and metering/actuation mechanisms to deliver the agent to a site of a medical procedure. The enclosure may include a sintered filter through which a pressurized fluid may pass. The agent may be received within a channel of the sintered filter. When the pressurized fluid passes through the sintered filter, it may enter the chamber having the agent at a variety of different vectors at the same time and may fluidize the agent. Aspects of the sintered filter and/or the metering/actuation mechanisms may facilitate flow of the pressurized fluid, even when the agent is not being delivered, which may assist in preventing or minimizing clogging during depressurization of the device.

Figure 1:
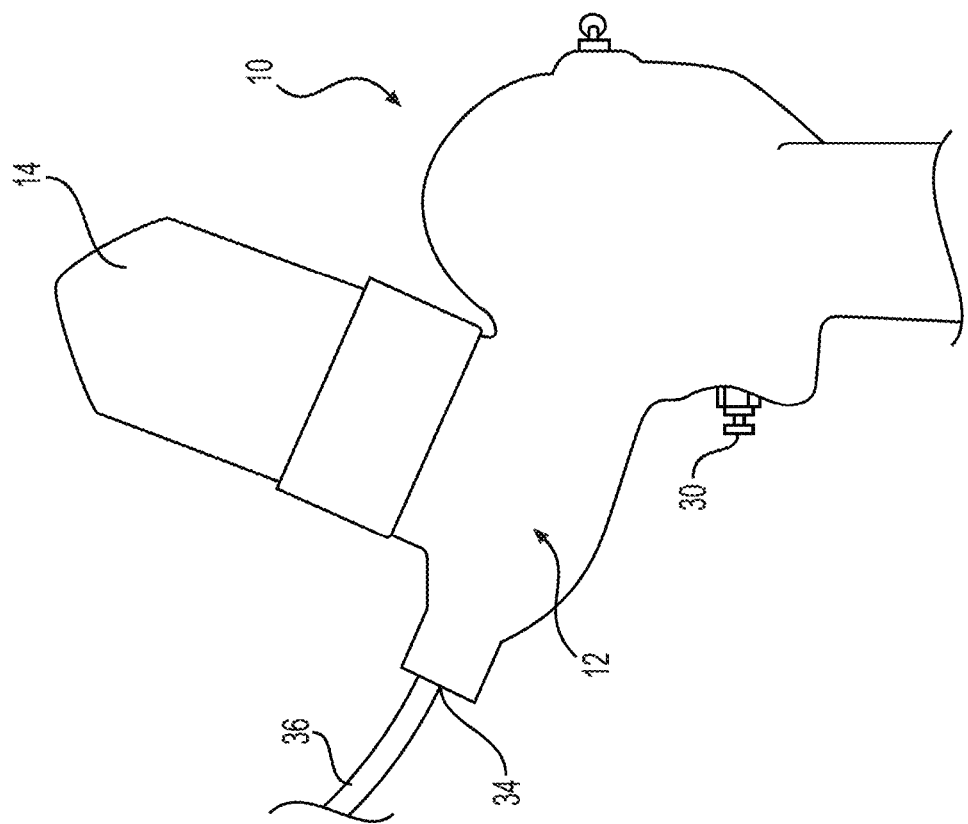
FIG. 1 shows an exemplary delivery device.

FIG. 1A shows a delivery system 10, which may be a powder delivery system. Delivery system 10 may include a body 12. Body 12 may include or may be configured to receive an enclosure 14 (or other source) storing an agent. Enclosure 14 may be coupled to body 12 for providing agent to body 12, or a lid/enclosure of the agent may be screwed onto, or otherwise coupled to, enclosure 14 for supplying the agent to enclosure 14. The agent may be, for example, a powdered agent, such as a hemostatic agent. The agent may alternatively be another type of agent or material or form of agent (e.g., a liquid or gel agent) and may have any desired function. Enclosure 14 may be removably attached to other components of delivery system 10, including components of body 12. Body 12 may have a variety of features, to be discussed in further detail herein. U.S. patent application Ser. No. 16/589,633, filed Oct. 1, 2019, the disclosure of which is hereby incorporated by reference in its entirety, discloses features of exemplary delivery devices and systems. The features of this disclosure may be combined with any of the features described in the above-referenced application. The features described herein may be used alone or in combination and are not mutually exclusive. Like reference numbers and/or terminology are used to denote similar structures, when possible.

An actuation mechanism 30 may be used to activate flow of a pressurized fluid and/or agent. Fluid alone or a combination of agent and fluid may be delivered from outlet 34 of body 12. As used herein, the terms "distal"/"first direction" may refer to a direction toward outlet 34 and away from enclosure 14, and the terms "proximal"/"second direction" may refer to the opposite direction. Outlet 34 may be in fluid communication with a catheter 36 or other component for delivering the combination of agent and fluid to a desired location within a body lumen of a patient.

Figure 2A:
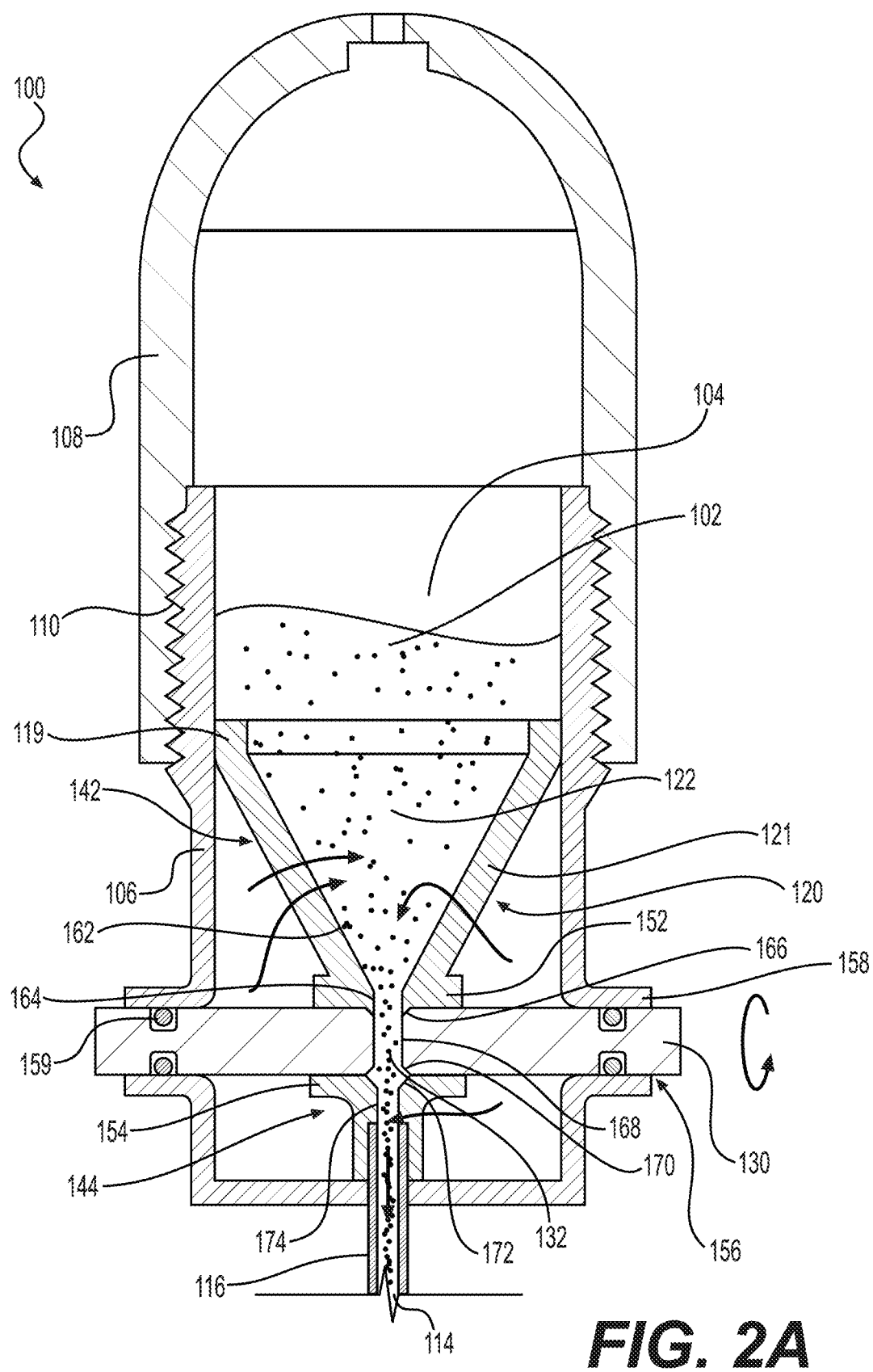
FIGS. 2A-5 show aspects of an exemplary enclosures for the delivery device of FIG. 1.
Figure 2B:
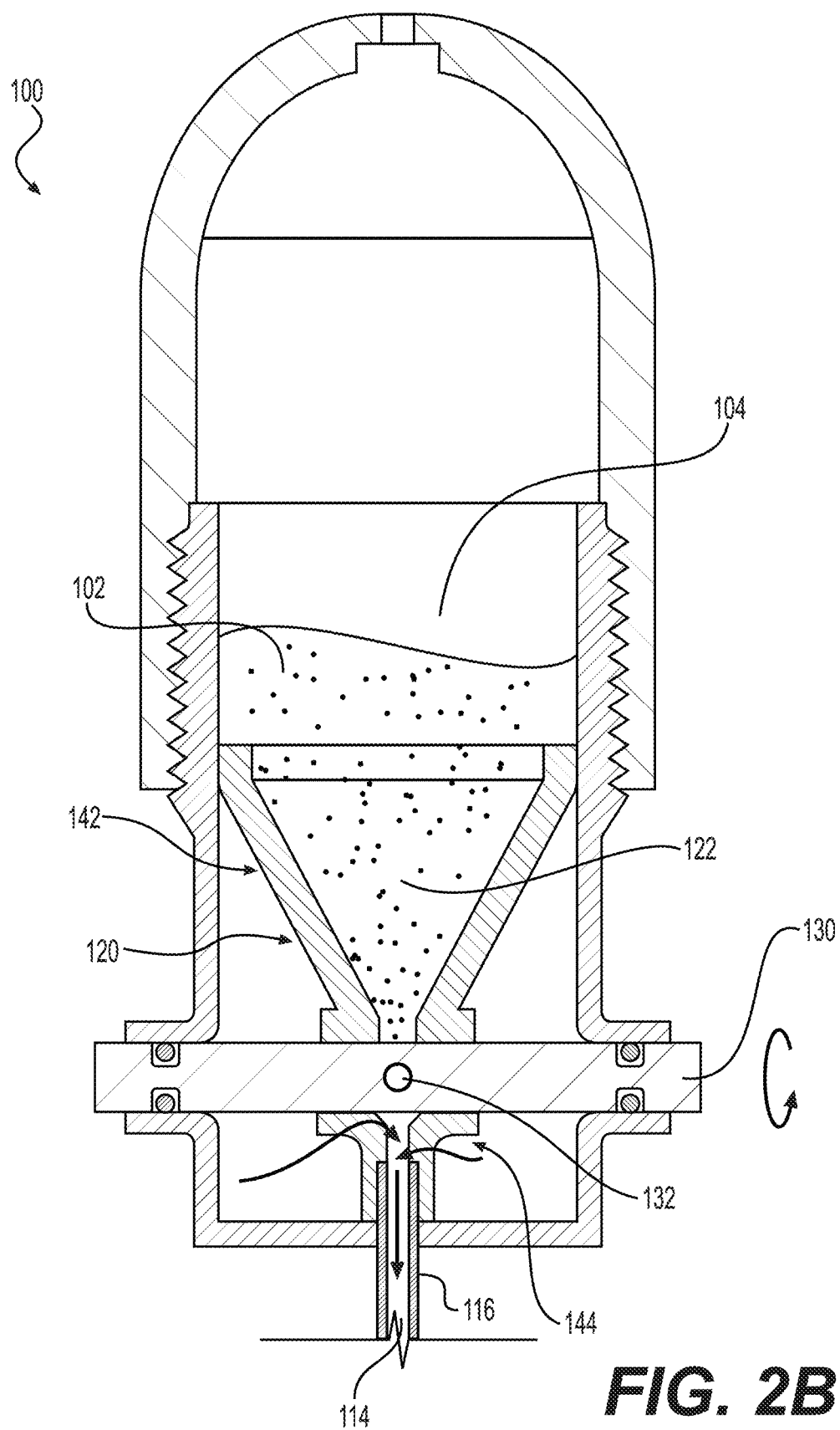
Figure 2C:
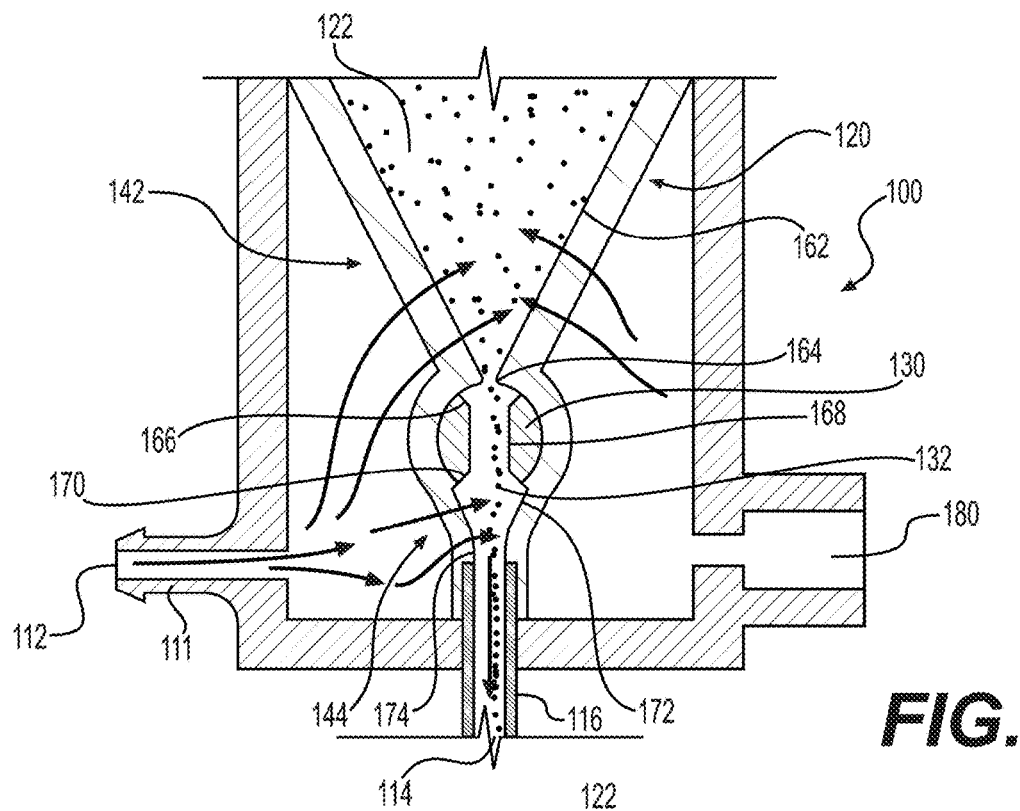
Figure 2D:
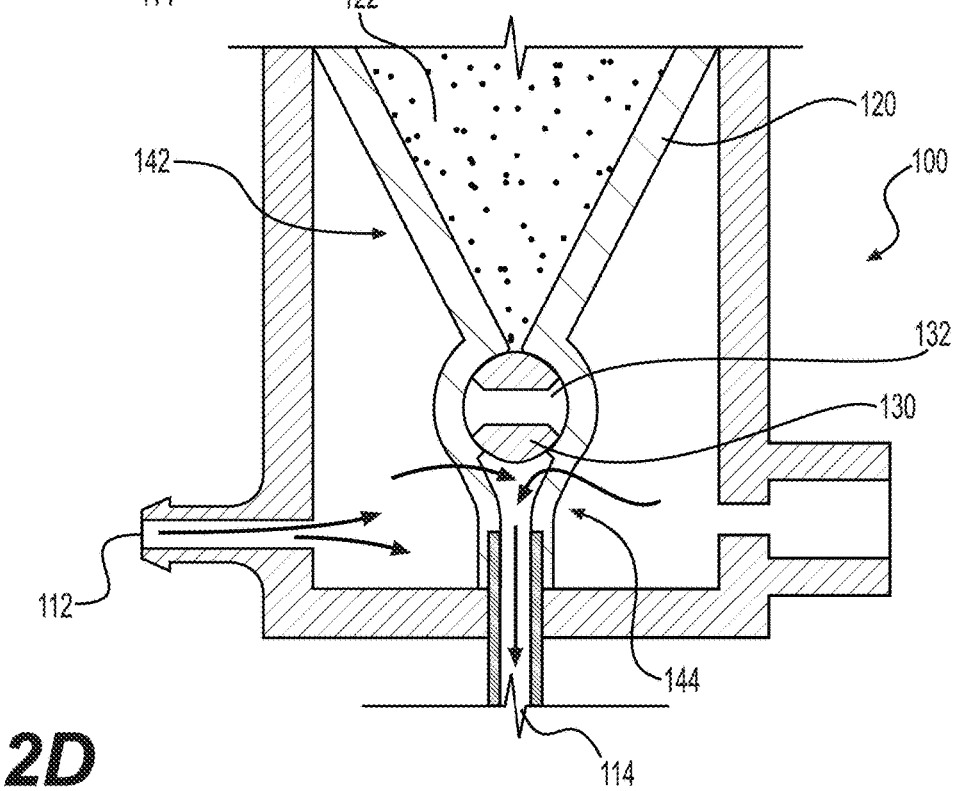
Figure 2E:
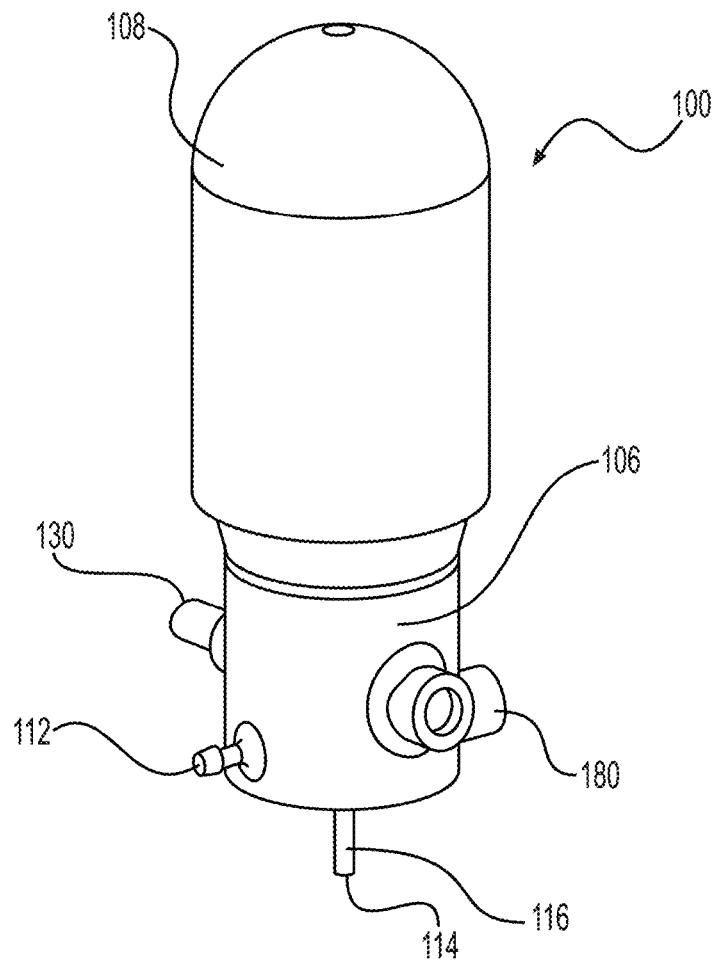

FIGS. 2A-2E show aspects of an example dispensing portion 100. Dispensing portion 100 may be used in place of enclosure 14 of delivery device 10. FIGS. 2A-2D show cross-sectional views, while FIG. 2E shows a perspective view. The views in FIGS. 2C and 2D are rotated ninety degrees with respect to the views of FIGS. 2A and 2B, respectively.

Dispensing portion 100 may include an enclosure 104 (which may have any of the properties of enclosure 14) that stores an agent 102. As shown in FIGS. 2A and 2B, Enclosure 104 may be defined by inner surfaces of a housing 106 and a lid 108. Housing 106 and/or lid 108 may include threads 110 enabling a distal end of lid 108 (a lower end, as shown in the Figures) to be screwed onto a proximal end of housing 106 (an upper end, as shown in the Figures). For example, an outer surface of housing 106 may include threads, and an inner surface of lid 108 may include threads.

Housing 106 may have a fluid inlet 112 (see FIGS. 2C and 2D). A wall of housing 106 may form a protrusion 111, which may define fluid inlet 112. Protrusion 111 may include a lip or other structure, which may assist with mating with tubing or other structures used to deliver fluid. Although fluid inlet 112 is shown at a side portion of housing 106, it will be appreciated that fluid inlet 112 may be in alternative locations. For example, fluid inlet 112 may be in a distal surface of housing 106 (the bottom of housing 106 in the Figures) or in lid 108. Housing 106 may also have an outlet 114. A catheter or other type of tubing 116 may define outlet 114, as described in further detail below. Outlet 114 may be in fluid communication with outlet 34 of delivery system 10.

A filter 120 may be disposed within a proximal portion of enclosure 104. Filter 120 may have a wall 121. In cross-sections of filter 120 along a longitudinal axis of filter 120, wall 121 may have a generally annular shape. An inner surface of wall 121 may define a channel 122. Agent 102 may be at least partially received within channel 122. Surfaces of wall 121 and surfaces of housing 106 may serve to form boundaries for agent 102.

Filter 120 and channel 122 may be substantially conical or funnel-shaped. At a proximal end of filter 120 (the top of filter 120 in the Figures), channel 122 may have its greatest diameter (perpendicular to a longitudinal axis of channel 122). Wall 121 may be angled such that, moving distally (toward the bottom of the Figures), channel 122 tapers to a smaller diameter. Further details regarding a shape of channel 122 are described below.

The proximal end of filter 120 may be sealed with respect to housing 106. For example, an outer surface of wall 121 may be sealed with respect to an inner surface of housing 106. Sealing may occur via, e.g., structures that are integrally formed with a remainder of filter 120, seals fitted on a remainder of filter 120 (e.g., O-ring seal(s)), and/or substances such as adhesives that secure filter 120 to housing 106. Because filter 120 is sealed with respect to housing 106, agent and/or fluid may not pass between an outer surface of wall 121 and an inner surface of housing 106 at a proximal end of filter 120. A distal end of filter 120 may also be sealed with respect to housing 106. For example, a distal end of filter 120 may be sealed with respect to an inner surface of a distal wall of housing 106 (the bottom wall in the Figures).

Figure 6A:
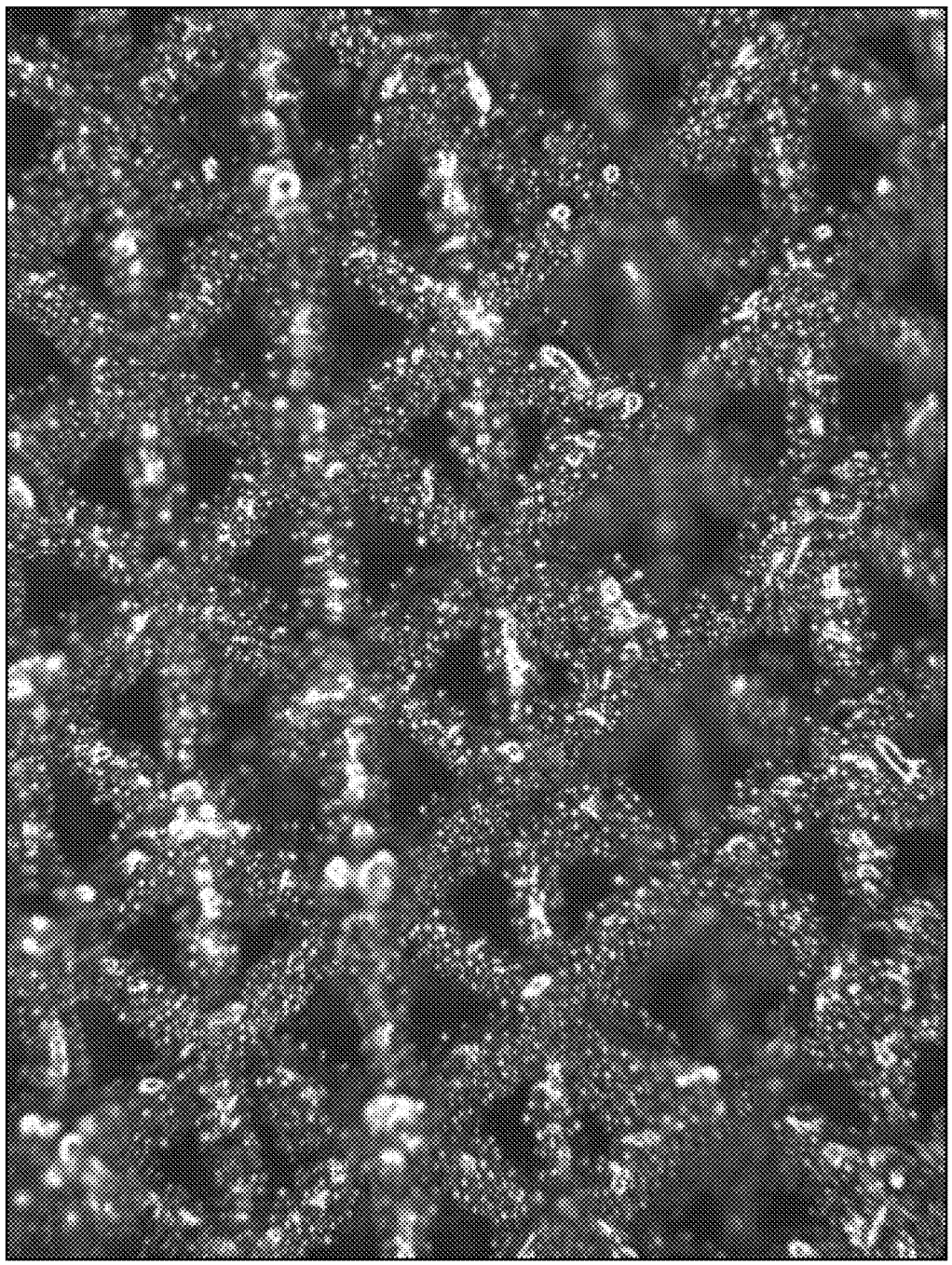
FIGS. 6A-6E depict exemplary filters for use with the enclosures of FIGS. 2A-5.
Figure 6B:
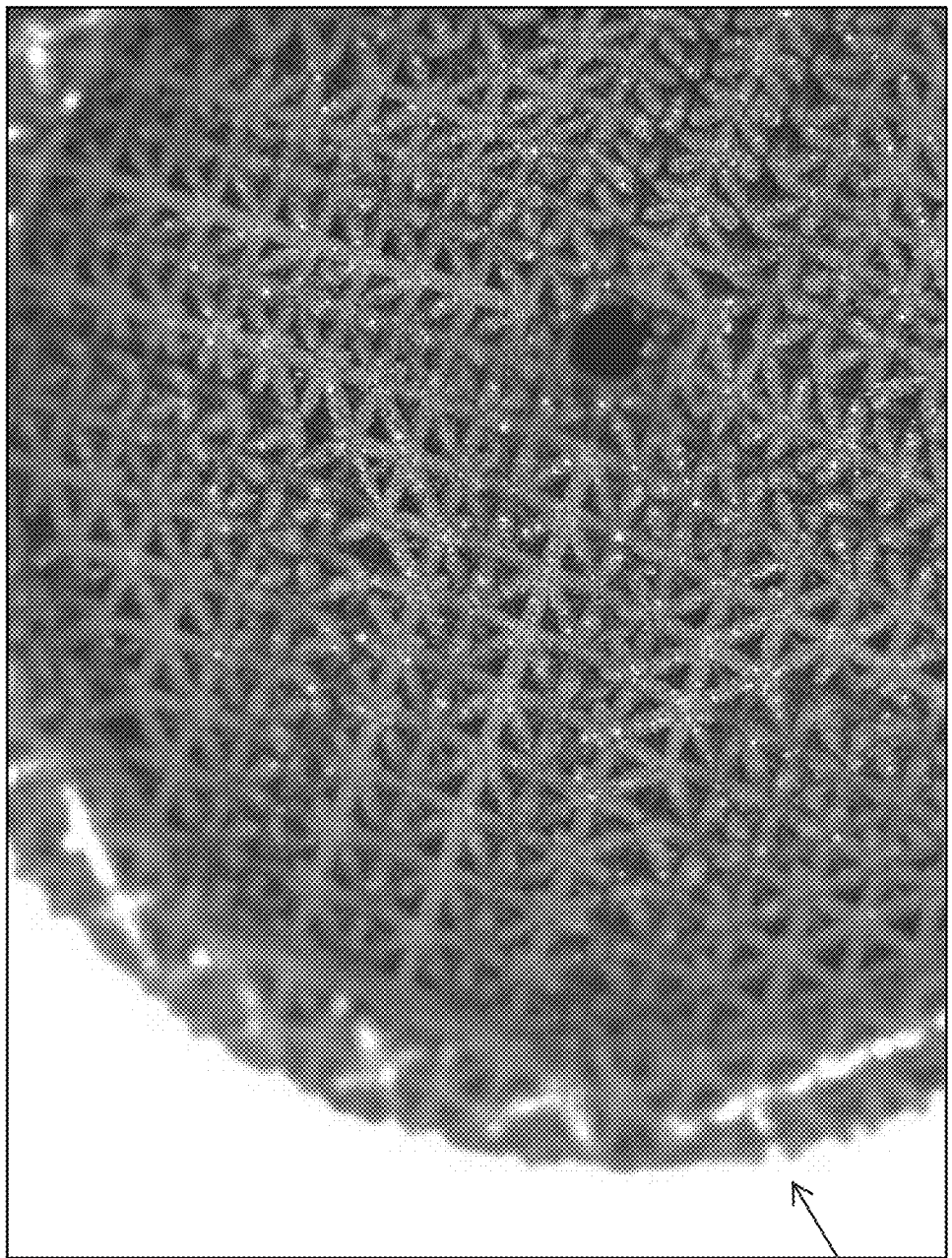
Figure 6C:
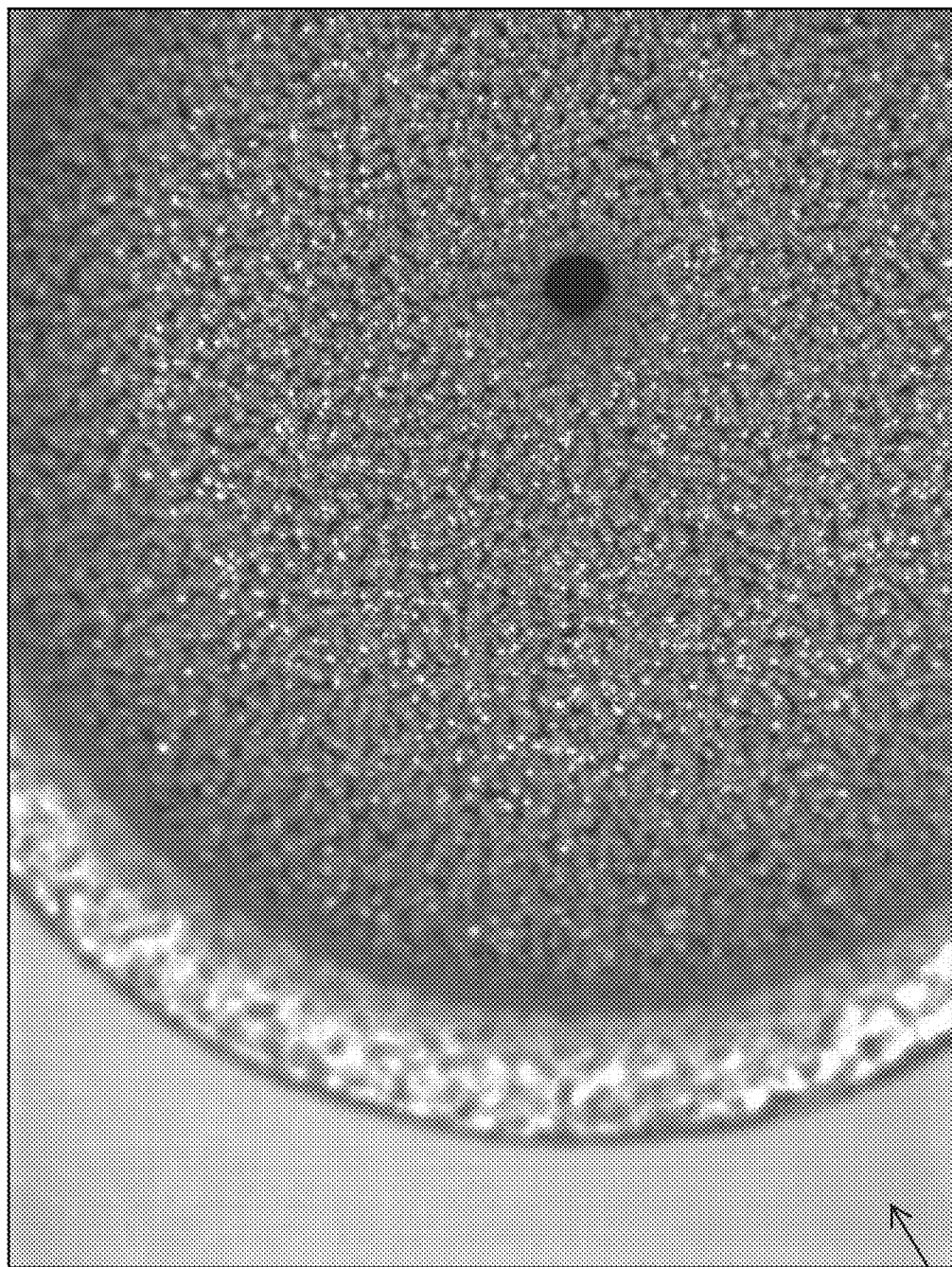
Figure 6D:
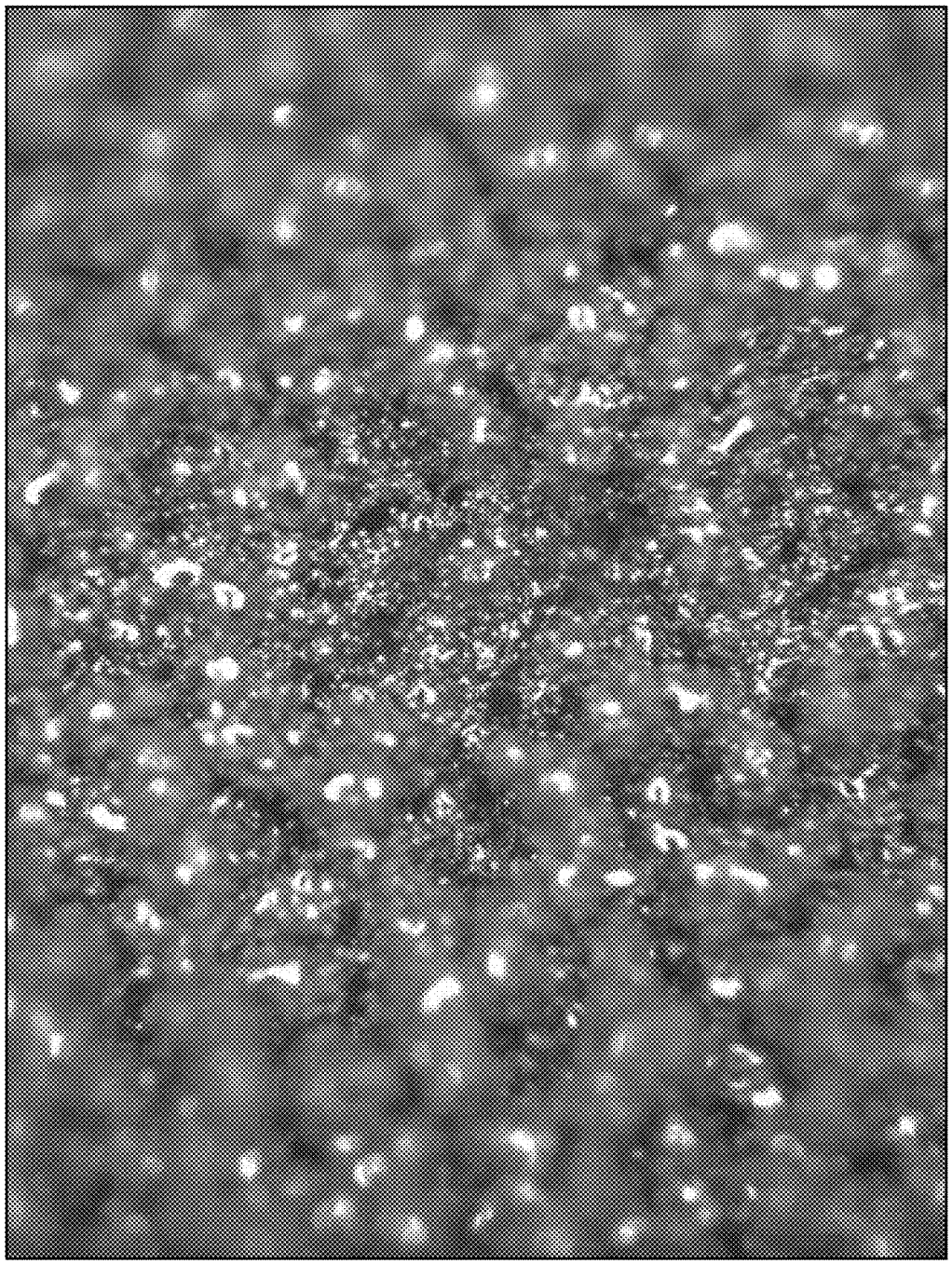
Figure 6E:
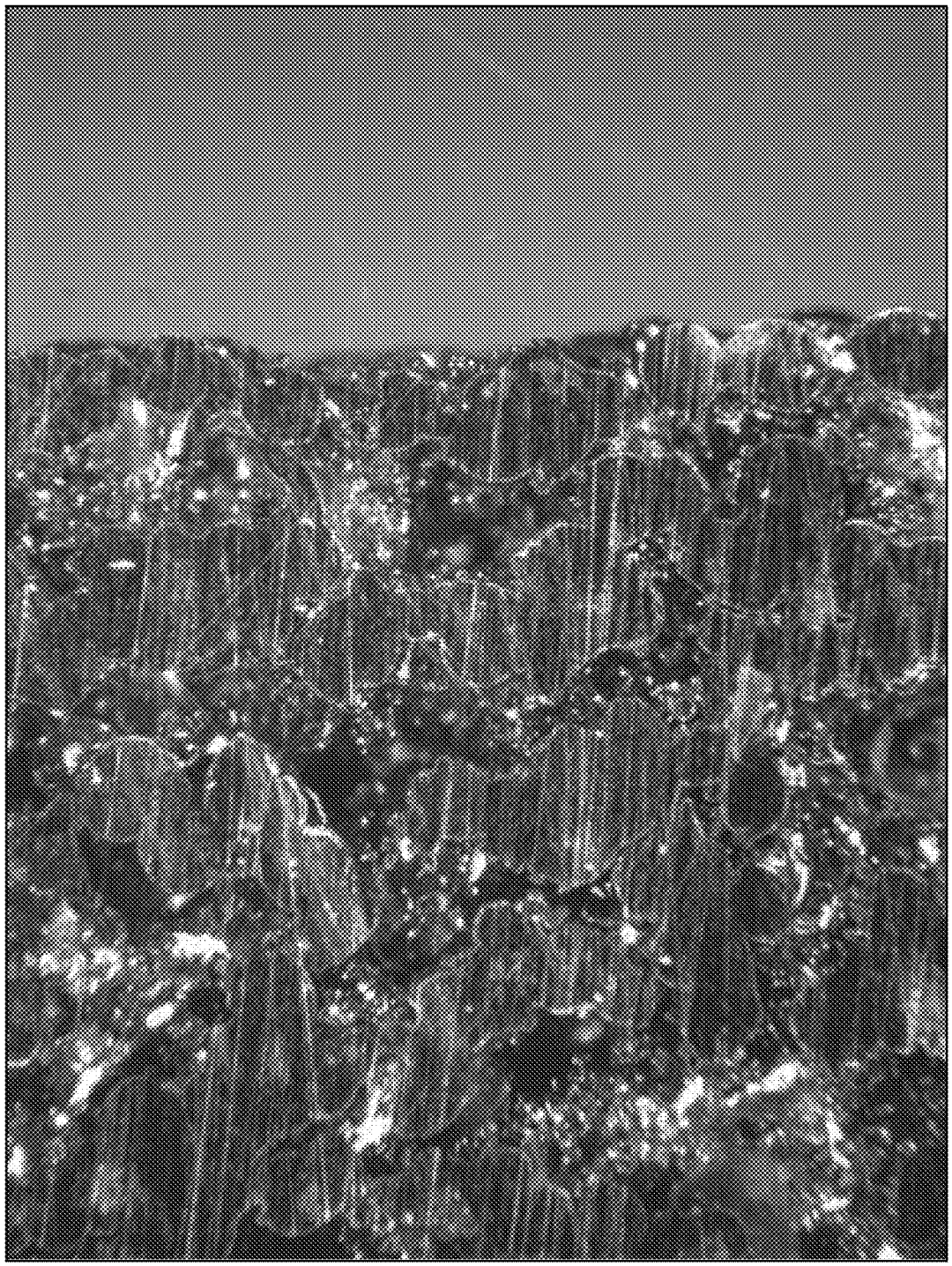

Wall 121 may have a constant thickness or a varying thickness. Wall 121 may be sintered, such that tortuous passages are formed between an outer surface of wall 121 and an inner surface of wall 121. The tortuous passages may be sized such that agent 102 does not pass through the passages between the inner surface and outer surface of wall 121. Fluid from fluid inlet 112 may be permitted to flow through the openings in wall 121, as described in further detail below. Openings may have sizes between approximately 40 microns and 150 microns (e.g., 100 microns). Particle sizes of agent 102 may range from approximately 200 microns to 600 microns (e.g., 320 microns to 400 microns). Filter 120 may be formed via, for example, additive manufacturing techniques (e.g., three-dimensional printing). For example, a pattern or model created to form filter 120 may incorporate sintered openings. Such openings may be formed by an algorithm that divides a model filter 120 into triangles or other shapes. FIGS. 6A and 6B show portions of a filter 120' made according to such an algorithm. FIG. 6A shows a zoomed-in portion of such a filter 120', while FIG. 6B shows a wider view of such a filter 120'. Other methods, such as triply periodic minimal surface ("TPMS") may alternatively be used to form gyroids, diamonds, or other shapes. The part may be printed using, for example, powder bed fusion methods (e.g., via electron beam or laser beam. Alternatively, a solid model of filter 120 may be created, and energy may be applied to form pores (passages) in wall 121. For example, a laser may be applied to a combination of metal powder and a foaming agent, which results in the development of pores/passages. Alternatively, a laser may be applied with energy calibrated so as to form pores as a metal powder is fused. FIGS. 6C-6E show examples of such a filter 120" made according to such laser-based methods. FIG. 6D shows a magnified version of FIG. 6C to show details of pores of filter 120". FIG. 6E shows a cross-sectional view of filter 120".

The tortuous passages of wall 121 may cause fluid flowing through filter 120 to enter channel 122 at a wide variety of vectors, including angles, velocities, and/or pressures at the same time. The fluid exiting wall 121 may have a turbulent flow pattern (e.g., a radial pattern). As also described below, the varying vectors with which fluid enters channel 122 may cause agent 102 within channel 122 to become fluidized. The turbulent flow of fluid (which may result in fluidization, such as a liquid sand effect, of agent 102) may aid in a flow of agent 102 through outlet 114 and may prevent or minimize clogging of agent 102. Fluidization may break up agglomerates of agent 102. Agent 102 may include, for example, semi-cohesive materials, such as chitosan acetate.

Catheter 116 or another component (e.g., tubing) may be received within a distal end of channel 122. For example, outer surfaces of catheter 116 may fit against the inner surface of wall 121. Catheter 116 may be fixed to filter 120 via adhesive, friction fit, ridges/grooves, or other suitable means. Catheter 116 may define outlet 114, which may be in fluid communication with outlet 34.

A rotatable shaft 130 may extend through enclosure 104 such that a longitudinal axis of shaft 130 is transverse to (e.g., substantially perpendicular to) a longitudinal axis of enclosure 104 and/or a proximal portion of catheter 116. In FIGS. 2C and 2D, shaft 130 is shown extending longitudinally into and out of the page.

An opening 132 may be formed in shaft 130. Opening 132 may extend through an entirety of shaft 130, substantially perpendicularly (or at least offset) to the longitudinal axis of shaft 130. Opening 132 may be substantially parallel to a longitudinal axis of enclosure 104 in some configurations (such as the configuration shown in FIG. 2C). As described in further detail below, in a first configuration of shaft 130 (FIGS. 2A, 2C), longitudinal axes of opening 132 and channel 122 may be aligned, such that fluid and/or agent 102 may pass from a portion of channel 122 that is proximal of shaft 130, through opening 132, and into a portion of channel 122 that is distal to shaft 130. In a second configuration of shaft 130, in which shaft 130 is rotated relative to the first configuration (FIGS. 2B, 2D), the longitudinal axis of opening 132 may be misaligned with respect to the longitudinal axis of channel 122, such that fluid and/or agent 102 does not pass between the portion of channel 122 that is proximal of shaft 130 into the portion of channel 122 that is distal to shaft 130, via opening 132. As shaft 130 is rotated, the longitudinal axes of channel 122 and opening 132 may align and misalign. For example, the longitudinal axes of channel 122 and opening 132 may be aligned with each 180 degree rotation of shaft 130.

Filter 120 may be configured so as to accommodate shaft 130. For example, cylindrical conduits 152, 154 of filter 120 may extend radially outward from a longitudinal axis of channel 122. Cylindrical conduits 152, 154 may have longitudinal axes that are parallel with the longitudinal axis of shaft 130. Shaft 130 may be received within cylindrical conduits 152, 154. In some examples, cylindrical conduits 152, 154 may together form a cylindrical conduit that has an opening forming channel 122 extending through the cylindrical conduit, transversely to a longitudinal axis of the cylindrical conduit. Cylindrical conduits 152, 154 and other surfaces of filter 120 may be configured so as to form a sleeve about shaft 130. Surfaces of shaft 130 may form a seal with inner surfaces of wall 121 such that agent 102 may not move distally past shaft 130 when shaft 130 is in the second configuration, and opening 132 is not in fluid communication with channel 122. The seal may be formed due to, for example, a material forming filter 120 and/or shaft 130. Shaft 130 may have the effect of dividing channel 122 into a proximal portion 142, proximal of shaft 130, and a distal portion 144, distal to shaft 130.

Shaft 130 may extend through openings 156 in sides of housing 106. Longitudinal axes of openings 156 may be substantially parallel to the longitudinal axis of shaft 130 and the longitudinal axes of openings 156 may be collinear with one another and/or with shaft 130. Protrusions 158 may extend around and define openings 156. A shape of protrusions 158 may be complementary to a shape of shaft 130. For example, protrusions 158 may have an annular or cylindrical shape. Seals 159 (e.g., O-ring seals) may be disposed about shaft 130 to create a seal between shaft 130 and inner surfaces of protrusion 158. Seals 159 may be disposed within circumferential grooves of shaft 130, as shown in the Figures, or may alternatively be disposed around a flush surface of shaft 130. Alternatively, seals 159 may be integrally formed with shaft 130. Seals 159 may prevent a flow of fluid and/or agent between shaft 130 and inner surfaces of protrusion 158.

Shaft 130 may have a first configuration, shown in FIGS. 2A and 2C, and a second configuration, shown in FIGS. 2B and 2D. In the first configuration (FIGS. 2A and 2C), agent 102 may flow through outlet 114. In the second configuration (FIGS. 2B and 2D), agent 102 does not flow through outlet 114 (i.e., agent 102 is prevented and/or blocked from flowing through outlet 114).

Prior to use of delivery system 10, shaft 130 may be in the second configuration of FIGS. 2B and 2D. In the second configuration, a longitudinal axis of opening 132 may be misaligned with or offset from channel 122 such that opening 132 is not in fluid communication with channel 122. Agent 102 cannot flow distally past shaft 130 and through outlet 114 because opening 132 is not in fluid communication with channel 122. Agent 102 may be retained within proximal portion 142 of channel 122 and other portions of enclosure 104.

Upon activation of actuation mechanism 30 or another actuation mechanism (transforming shaft 130 to the first configuration), fluid may be permitted to flow through fluid inlet 112 (see FIGS. 2C-2E). The fluid from fluid inlet 112 may pass through sintered portions of wall 121 of distal portion 144 of filter 120. The fluid may flow into channel 122, into catheter 116, and out of outlet 114. The fluid from inlet 112 may also pass through sintered portions of wall 121 into proximal portion 142 of channel 122. However, while shaft 130 remains in the second configuration, agent 102 may not flow into opening 132 to the portion of channel 122 in distal portion 144 of filter 120. The arrows in FIGS. 2A and 2C show the flow of fluid in the first configuration, while fluid flows through fluid inlet 112.

When shaft 130 is rotated to the first configuration (FIGS. 2A and 2C), via actuation mechanism 30 or via a separate actuator, agent 102 may be permitted to flow through channel 122, to distal portion 144. Fluid may continue to flow through wall 121 of filter 120, as described above, into proximal portion 142 and distal portion 144. The fluid flowing into channel 122 (e.g., into proximal portion 142) may fluidize agent 102.

An inner surface of wall 121 and a surface defining opening 132 may be shaped such that channel 122 and opening 132 have a varying diameter between a proximal end of channel 122 and a distal end of channel 122. As agent 102 moves distally, it encounters portions of channel 122 that vary in diameter, which reduces clogging of agent 102 within channel 122. Agent 102 may be prone to bridging, which may result in clogging absent the variations in diameter of channel 122.

As described above, at a first, proximal portion 162 of channel 122, an inner surface of wall 121 may taper inward, moving in a distal direction. An angle of first portion 162 may be greater than (i.e., steeper than) an angle of repose of agent 102. An angle of repose of agent 102 may be an angle formed by a cone-like pile of agent 102 as agent 102 flows through an orifice and collects on a surface in the cone-like pile. The angle of repose may be the angle between the surface onto which the agent 102 flows and a surface of the cone-like pile. The angle of repose may be related to friction or resistance to movements between particles of agent 102. Because wall 121 may have an angle greater than the angle of repose of agent 102, agent 102 may flow freely through funnel channel 122, due to a force of gravity.

Just proximally of shaft 130, at a second portion 164 of channel 122, the inner surface of wall 121 may have a constant diameter. A proximal end of opening 132 may be narrower (e.g., slightly narrower) than the portion of channel adjacent to the proximal end of opening 132. Alternatively, a proximal end of opening 132 may have substantially the same width as or a greater width than the portion of channel 122 that is adjacent and proximate to opening 132.

Opening 132 may have first portion 166, second portion 168, and third portion 170. In first portion 166, the inner surface of shaft 130 may taper radially inward moving in a distal direction such that a size of opening 132 decreases. In second portion 168, opening 132 may have a constant or substantially constant diameter. In third portion 170, the inner surface of shaft 130 may taper radially outward moving in the distal direction, such that the size of opening 132 increases. A distal end of opening 132 may have a size that is the same as or substantially the same as the size of channel 122 adjacent to the distal end of opening 132.

Distally of the distal end of opening 132, a third portion 172 of channel 122 may be defined by inner surfaces of wall 121 that taper inward moving distally to a fourth portion 174 of channel 122, which may have a constant diameter. The diameter of fourth portion 174 may be substantially the same as an inner diameter of catheter 116.

In passing through channel 122, agent 102 first travels through a narrowing portion (first portion 162), through a constant diameter portion (second portion 164), through a wider portion (a proximal end of opening 132), into a narrowing portion (first portion 166), through a constant diameter portion (second portion 168), through a widening portion (third portion 170), through a narrowing portion (third portion 172), and then through a constant diameter portion 174, into catheter 116. These alternating widening and narrowing segments of passage 122 and opening 132 may result in decreased clogging of agent 102 in some embodiments due to, for example, a reduction in bridging of agent 102. Portions of channel 122 that are tapering and/or angled may have an angle of approximately 45 degrees.

Following a desired flow of agent 102, shaft 130 may be transitioned from the first configuration to the second configuration, so that agent 102 is no longer capable of flowing through outlet 114. Fluid may continue to flow from inlet 112 through outlet 114, as described above. Such continued fluid flow may help purge agent delivery device 10.

During flow of fluid, enclosure 104 may become pressurized. Aspects of dispensing portion 100 may facilitate depressurization of enclosure 104, in particular, while shaft 130 is in the second configuration. Were agent 102 permitted to flow out of outlet 114 during depressurization, agent 102 may exit outlet 114, which may lead to clogging of agent delivery device 10. Filter 120 and shaft 130 allow enclosure 104 to depressurize without a risk of agent 102 being drawn out of exit 114 when shaft 130 is in the second configuration. Fluid may flow out of outlet 114 without a flow of agent 102, because shaft 130 does not permit passage of agent 102 through outlet 114.

Dispensing portion 100 may also include a release valve 180 (FIG. 2E). Release valve 180 may provide a mechanism for depressurizing chamber 104. For example, release valve 180 may be particularly helpful in circumstances in which pressure requires emergency release (e.g., during a procedure). Release valve 180 may also provide a mechanism for depressurizing enclosure 104 during the ordinary course of a procedure. Release valve 180 may be used in addition to or in alternative to the depressurizing mechanics described above. A relief pressure may be approximately 60 pounds per square inch gauge (PSIG).

Dispensing portion 100 may provide numerous benefits in certain embodiments. For example, filter 120 can provide for a turbulent flow of fluid as it combines with agent 102. The turbulent flow of fluid may provide improvements to flow of agent 102 through outlet 34 as compared to devices without filter 120 and/or devices that do not allow for turbulent flow. Dispensing portion 100 also may allow depressurization of enclosure 104 without a flow of agent 102 into distal portions of delivery device 10. The configuration of channel 122 and opening 132 may facilitate delivery of agent 102 without clogging (or without significant clogging) due to, for example, bridging of agent 102.

Figure 3A:
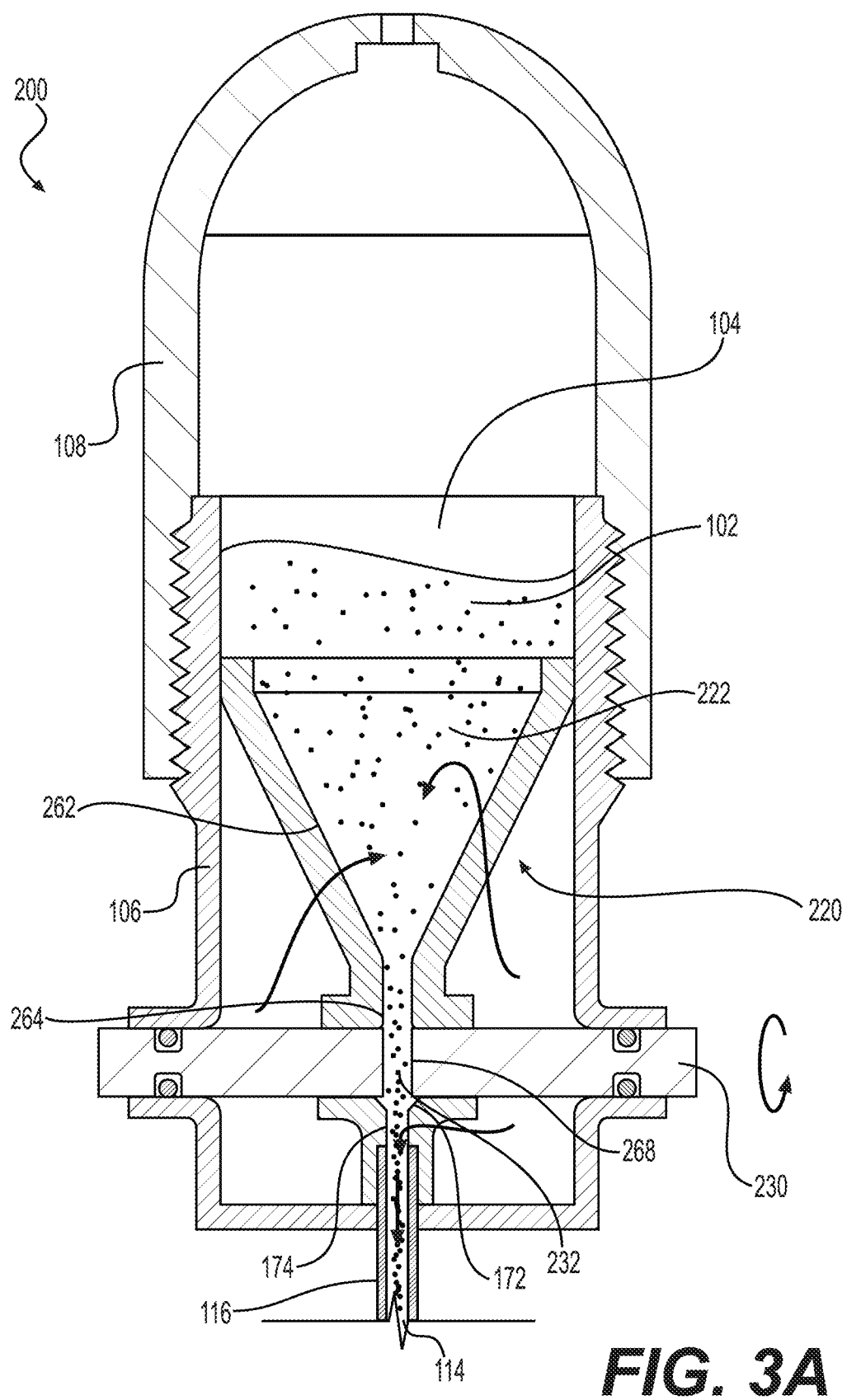

FIG. 3A shows an alternative dispensing portion 200. Dispensing portion 200 may have any of the properties of dispensing portion 100, except where noted specifically herein. Like reference numbers are used where practical. Aspects of dispensing portion 200 may be combined with aspects of dispensing portion 100 and are not mutually exclusive.

Enclosure 104 may include a filter 220 disposed therein. Filter 220 may be manufactured according to the same techniques as filter 120 and may include the same type of material and the same type of tortuous passages. A shape of filter 220 may differ from a shape of filter 120. A distal end of filter 220 (the top end in FIG. 3A) may extend further proximally in enclosure 104 as compared to filter 120.

A rotatable shaft 230 may extend through enclosure 104 such that a longitudinal axis of shaft 230 is transverse to (e.g., substantially perpendicular to) a longitudinal axis of enclosure 104 and/or a proximal portion of catheter 116. Rotatable shaft 230 may have any of the properties of rotatable shaft 130. A shape of an opening 232 extending through shaft 230, substantially perpendicularly to the longitudinal axis of shaft 230, may differ from the shape of opening 132 of shaft 130.

Inner surfaces of walls 221 of filter 220 may define a channel 222. In a first, proximal portion 262 of channel 222, an inner surface of wall 221 may taper inward toward a distal direction (the bottom of FIG. 3A). An angle between a surface defining first portion 262 may be greater than an angle of repose of agent 102 (e.g., the angle may be steeper than the angle of repose). Agent 102 may flow freely through portion 262 due to a force of gravity.

Proximally of shaft 230, at a second portion 264 of channel 222, the inner surface of wall 221 may extend in a direction that is substantially parallel to a longitudinal axis of channel 222. Second portion 264 may have a tubular shape, with a substantially constant diameter.

Opening 232 may have a tubular shape, with a substantially constant diameter. Opening 232 may have substantially the same diameter as second portion 264. Alternatively, a proximal end of opening 232 may have a greater or smaller width than second portion 264. A distal end of opening 232 may have a size that is the smaller than the size of channel 222 adjacent to the distal end of opening 232.

Distally of shaft 230, channel 222 may have the same shape as channel 122, described above. As noted above, the features of dispensing portions 100 and 200 are not mutually exclusive. For example, filter 120 may be utilized with shaft 230, and filter 220 may be utilized with shaft 130.

When shaft 230 is in a configuration allowing a flow of agent 102 through opening 232 (as shown in FIG. 3A), agent 102 may travel through a progressively smaller channel 222 as it travels distally within portion 262, until it reaches portion 264, in which a diameter of channel 222 is constant. Agent 102 may continue to pass through a region of constant diameter through opening 232. Distal to opening 232, agent 102 may encounter a larger diameter portion of passage 222 at a proximal end of portion 172. A diameter of passage 222 may taper distally at portion 172, until powder 102 encounters the constant diameter segment of passage 222 in portion 174.

As with passage 122 and opening 132, passage 222 and opening 232 may be configured to avoid clogging of agent 102 due to, for example, bridging of agent 102 across passage 222/opening 232. Aside from a shape of passage 232, fluid and agent 102 may flow as described above with respect to FIGS. 2A-2E. The configuration of FIG. 3A may allow agent 102 to pass through a consistent diameter through second portion 264 and opening 232. The sintered, neck-like structure of second portion 264 may assist with keeping agent 102 moving and fluidized through a narrowest section of the system.

Figure 3B:
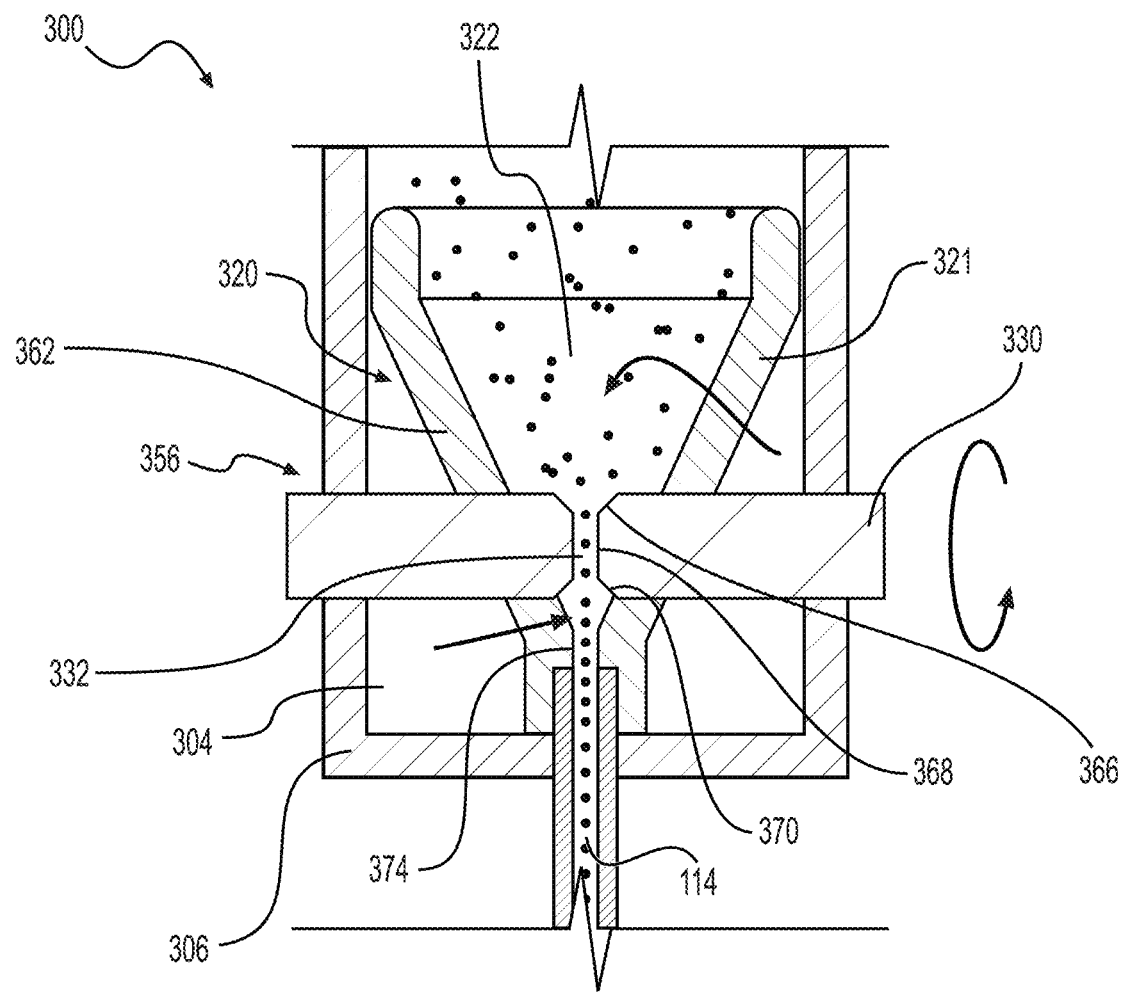

FIG. 3B shows a portion of another dispensing portion 300. Dispensing portion 300 may have any of the properties of dispensing portions 100 or 200, except where noted specifically herein. Like reference numbers are used where practical. Aspects of dispensing portions 100, 200, and/or 300 may be combined in various combinations and are not mutually exclusive.

Dispensing portion 300 may include a housing 306, which may have any of the properties of housing 106, except as specified herein. Housing 306 may define an enclosure 304, which may have any of the properties of enclosure 104.

Enclosure 304 may include a filter 320 disposed therein. Filter 320 may be manufactured according to the same techniques as filters 120, 220 and may include the same type of material and the same type of tortuous passages. A shape of filter 320 may differ from a shape of filters 120, 220. Filter 320 may include a wall 321. An inner surface of wall 321 may define a channel 322, which may receive agent 102. Filter 320 may be sealed relative to an inner surface of housing 306, as described above with respect to filter 120 and housing 106.

A rotatable shaft 330 may extend through enclosure 104 such that a longitudinal axis of shaft 330 is transverse to (e.g., substantially perpendicular to) a longitudinal axis of enclosure 304 and/or a proximal portion of catheter 116. Rotatable shaft 330 may have any of the properties of rotatable shafts 130, 230. A shape of an opening 332 is shown as being the same as that of opening 132. First portion 366 may have any of the properties of first portion 166, second portion 368 may have any of the properties of second portion 168, and third portion 370 may have any of the properties of third portion 170. Alternatively, opening 332 may have a shape like that of opening 232 or may have an alternative shape. FIG. 3B shows rotatable shaft 330 in a configuration in which agent 102 is permitted to pass distally through opening 332 and outlet 114.

Shaft 330 may extend through collinear openings 356 in housing 306. Housing 306 may not include structures corresponding to protrusions 158 but instead may include openings disposed through and flush with a surface of housing 106. Shaft 330 may not include structures corresponding to seals 159. Alternatively, housing 306 may be configured like housing 106 and may include protrusions 158 and/or shaft 330 may include seals 159. Alternatively, other structures may be used in any of dispensing portions 100, 200, and/or 300 to seal shaft 130, 230, and/or 330 relative to enclosure 104 and/or 304.

Channel 322 may include a tapered portion 362 (proximally and distally of shaft 330) and a straight portion 374 (distally of shaft 330). An angle of a surface defining first portion 362 may be greater than (i.e., steeper than) an angle of repose of agent 102. Agent 102 may flow freely through portion 362 due to a force of gravity. Straight portion 374 may be, for example, tubular. Shaft 330 may extend through tapered portion 362. Filter 320 is shown as lacking structures corresponding to cylindrical conduits 152, 154. Alternatively, filter 320 may include structures similar to protrusions 152.

As agent 102 moves distally through channel 322, agent 102 may first pass through tapered portion 362 until it reaches opening 332. A proximal end of opening 332 may be narrower than a portion of channel 322 adjacent to the proximal end of opening 332. Within opening 332, agent 102 may pass through first portion 366, which tapers inward distally, until it reaches second portion 368, which may have a constant diameter. Agent 102 may then pass through third portion 370, which may have a width that tapers outward in the distal direction.

A portion of channel 322 adjacent to a distal end of opening 332 may have substantially the same width as the distal end of opening 332. The agent 102 may continue to pass through tapered portion 362, until it reaches straight portion 374. A width of straight portion 374 may be the same as an internal diameter of catheter 116. Agent 102 may pass from straight portion 374 into catheter 116 and through outlet 114.

As with passages 122, 222 and openings 132, 232, passage 322 and opening 332 may be configured to avoid clogging of agent 102 due to, for example, bridging of agent 102 across passage 322/opening 332. Aside from a shape of passage 332, fluid and powder 102 may flow as described above with respect to FIGS. 2A-2E.

Figure 4A:
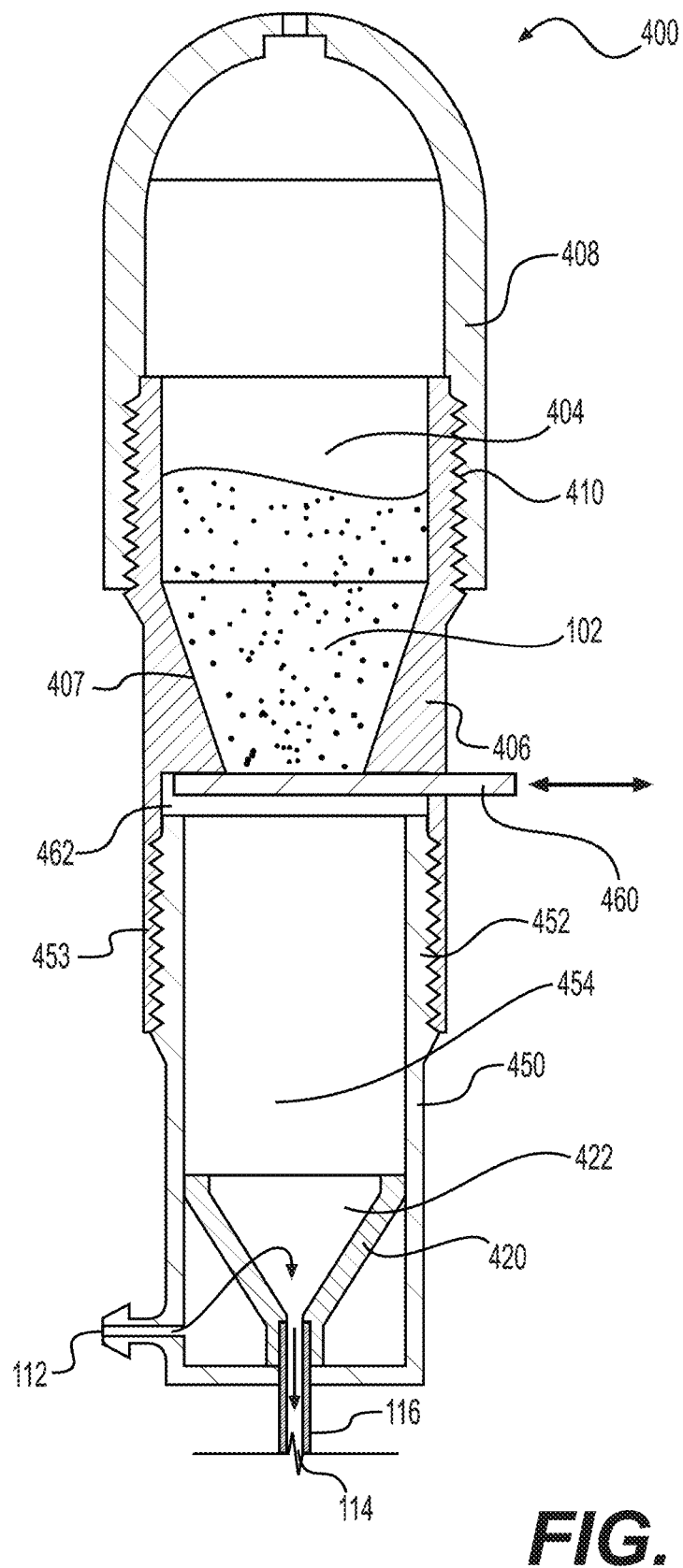
Figure 4B:
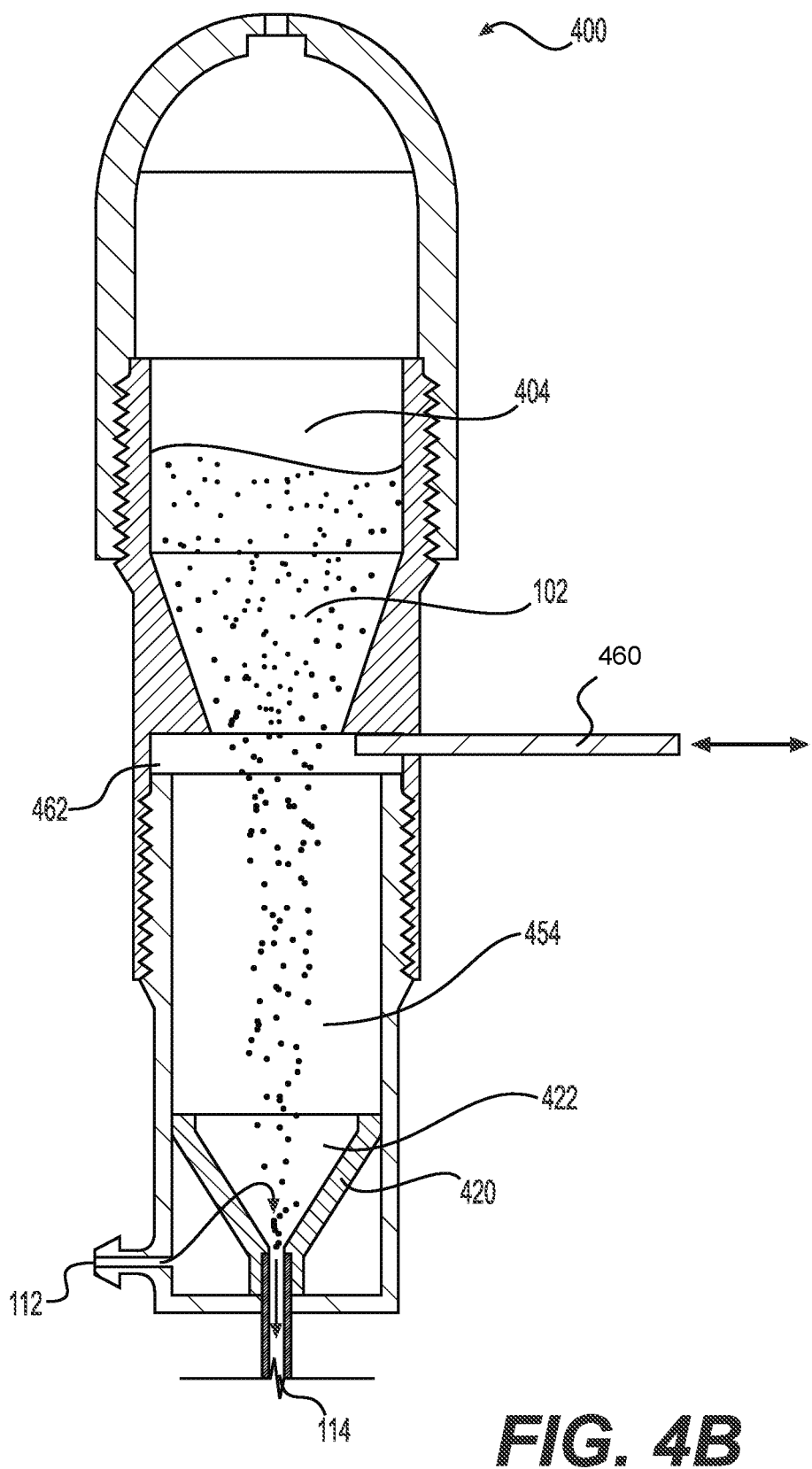

FIGS. 4A and 4B show an alternative dispensing portion 400. Dispensing portion 400 may have properties of dispensing portions 100, 200, 300, described above, except where as specified below. Aspects of dispensing portion 400 may be combined with aspects of dispensing portions 100, 200, 300, described above.

Dispensing portion 400 may include a first housing 406, which may have any of the properties of housings 106, 306, except as specified herein. A lid 408, which may have any of the properties of lid 108, may be retained on first housing 406 via threads 410.

Housing 406 may define a first enclosure 404, which may have any of the properties of enclosures 104, 304. Agent 102 may be stored within first enclosure 404. Inner surfaces of walls of housing 406 may define a funnel 407. An angle of funnel 407 may be greater (i.e., steeper than) than an angle of repose of agent 102. Agent 102 may flow freely through funnel 407 due to a force of gravity.

Housing 406 may be disposed proximally of a second housing 450. Second housing 450 may include walls 452. Walls 452 may be partially received within a rim 453 of first housing 406. An inner surface of rim 453 and an outer surface of walls 452 may each include threads, which may be used to mate rim 453 with walls 452. Second housing 450 may define a second enclosure 454. Second housing 452 may have fluid inlet 112.

A filter 420 may be received within a distal portion of enclosure 454. Filter 420 may have the properties of any of filters 120, 220, 320. A proximal end and a distal end of filter 420 may be sealed with respect to inner surfaces of second housing 450 defining enclosure 454, using any of the mechanisms described above with respect to filter 120. Filter 420 may have a substantially funnel shape, defining a channel 422. Catheter 116 may be received within channel 422 and may define outlet 114.

First housing 406 may define an opening 462 near a distal end of housing 406. Opening 462 may extend in a plane substantially perpendicular to a longitudinal axis of enclosures 104, 454. A slider 460 (e.g., a plate) may be received within opening 462 and may be movable in the plane of opening 462 (perpendicular to a longitudinal axis of enclosures 404, 454). Activation of actuation mechanism 30 or another actuation mechanism may cause slider 460 to transition between a first configuration (FIG. 4A) and a second configuration (FIG. 4B).

In the first configuration (FIG. 4A), slider 460 may intercept and/or cover a distal end of enclosure 404, such that first enclosure 404 is not in fluid communication with enclosure 454. Slider 460 and/or first enclosure 404 may include seals that prevent passage of agent 102 and/or fluid proximally or distally past slider 460 when slider 460 is in the first configuration. In the first configuration, when a flow of fluid is activated (e.g., via actuation mechanism 30), fluid may pass through inlet 112, through sintered portions of a wall of filter 420, into channel 422. Fluid may then pass into catheter 116 and through outlet 114.

In the second configuration (FIG. 4B), slider 460 does not intercept or enclose (or at least partially does not intercept or enclose) the distal end of enclosure first 404. Therefore, first enclosure 404 may be in fluid communication with second enclosure 454, and agent 102 may flow from first enclosure 404 into second enclosure 454 in the second configuration. Agent 102 may enter channel 422, where agent 102 may combine with fluid from inlet 112. The fluid may fluidize agent 102. Agent 102, combined with the fluid, may pass through catheter 116 and through outlet 114.

In operation, a user may activate actuation mechanism 30, which may activate only a flow of fluid through inlet 112 or may activate a flow of fluid through inlet 112 and transition slider 460 from the first configuration to the second configuration. Alternatively, separate actuation mechanisms may be used to activate a flow of fluid through inlet 112 and to transition slider 460 from the first configuration to the second configuration. After slider 460 transitions to the second configuration, agent 102 may begin flowing through outlet 114, as described above.

Following a delivery of a desired amount of agent 102, slider 460 may be transitioned from the second configuration to the first configuration, stopping a flow of agent 102 through outlet 114. A flow of fluid may or may not continue after slider 460 has been transitioned to the first configuration. As described above with respect to dispensing portion 100, dispensing portion 400 may facilitate depressurization of chamber 454. Because agent 102 is barred from entering chamber 454 in the second configuration of slider 460, chamber 454 may be depressurized (pressurized fluid may exit outlet 114) without agent 102 being drawn through outlet 114. An ability to depressurize chamber 454 without drawing agent 102 through outlet 114 may prevent or minimize clogging of agent 102.

Figure 5:
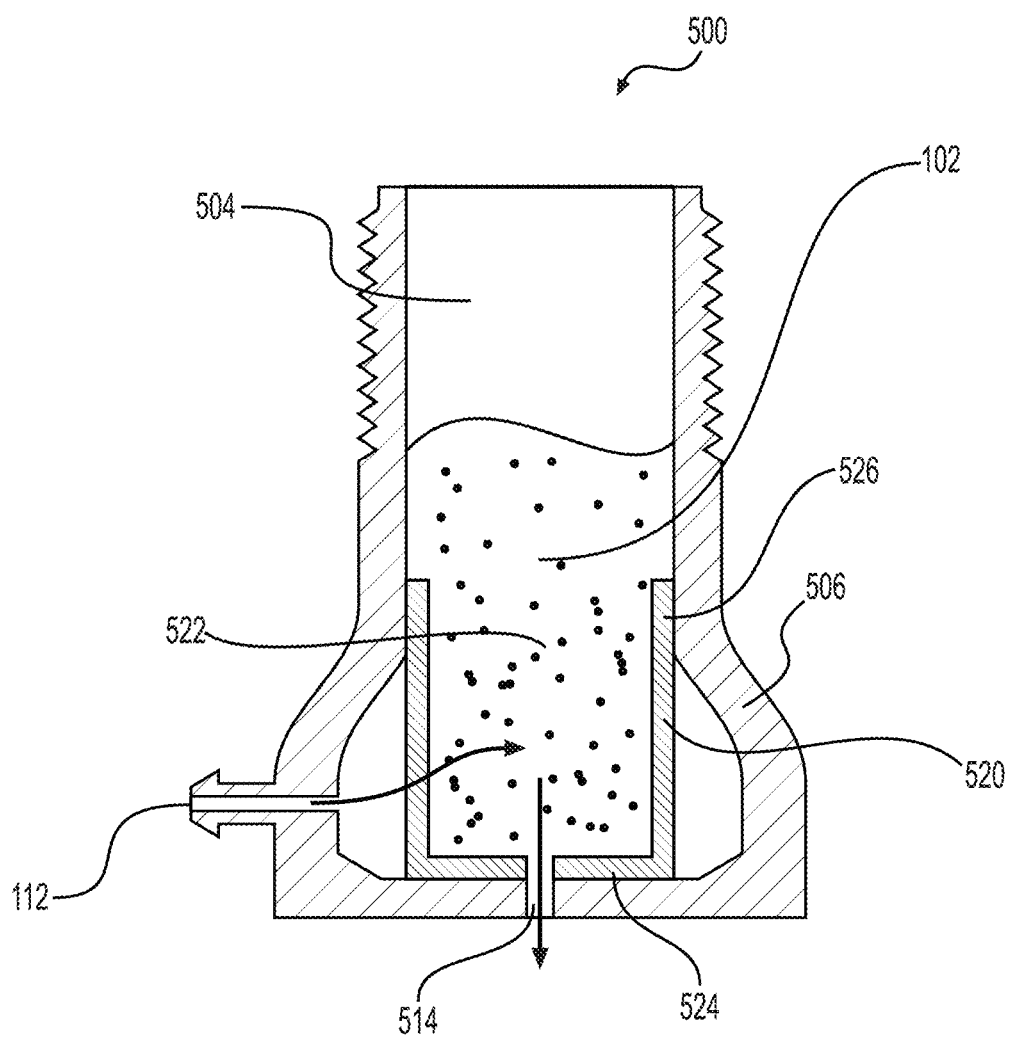

FIG. 5 shows portions of an alternative dispensing portion 500. Dispensing portion 500 may have features of dispensing portions 100, 200, 300, 400, described above. Dispensing portion 500 may include a housing 506, which may have any of the features of housing 106. Housing 506 may receive a lid (not shown), such as lid 108. Housing 506 may define an enclosure 504. A fluid inlet 112 and an outlet 514 may be in fluid communication with housing 506.

A filter 520 may be received within a distal portion of housing 506. Filter 520 may have properties of filter 120, including the material properties of filter 120 and the tortuous passages formed therein. Proximal ends of filter 520 may be sealed relative to inner surfaces of 506, by, for example, the mechanisms described above with respect to filter 120. Filter 520 may be cylindrical and/or cup-shaped. Filter 520 may have a flat, distal wall 524 (a bottom surface, shown in FIG. 5) and a cylindrical wall 526. Filter 520 may define a channel 522. Agent 102 may be received within channel 522 and other portions of enclosure 504. An opening may be formed in distal wall 524, which may be in fluid communication with outlet 514. Although a structure corresponding to catheter 116 is not shown in FIG. 5, it will be appreciated that a catheter such as catheter 116 may be received within outlet 514 and/or the opening in distal wall 524.

In operation, a flow of fluid through inlet 112 may be activated. The fluid may pass through the walls of filter 520 (e.g., cylindrical wall 526). Where, as discussed, above, inlet 112 is disposed on a distal surface of enclosure 504, the fluid from inlet 112 may be piped through a cavity on the bottom of filter 520 (not shown). The fluid may have an exit filter 520 simultaneously along a variety of vectors, as described above (e.g., with respect to filter 520). The fluid may combine with agent 102 and may fluidize agent 102. The combined fluid and agent 102 may pass through outlet 514.

As discussed above, filters 120, 220, 320, 420, 520 may have sintered walls, with openings/pores formed therethrough. Alternatively, instead of a sintering process, the walls of the filters may be made porous through any other suitable process, including, for example, a three-dimensional (3D) printing process. The following description provides examples of pore sizes of filters 120, 220, 320, 420, 520 and particle dimensions/sizes of agent 102. Pores of filters 120, 220, 320, 420, 520 may have sizes ranging from approximately 2 microns to approximately 100 microns (e.g., 40 microns or 100 microns). A size of the pores may be substantially uniform or may vary. As described above, the varying, simultaneous vectors of fluid passing through walls of filters 120, 220, 320, 420, 520 may cause agent 102 to become fluidized (e.g., may have a liquid sand effect). Fluidization of agent 102 may have various advantages, including aerating agent 102, reducing friction between particles of agent 102, suspending particles of agent 102 in fluid (e.g., air or carbon dioxide) to propel them, faster delivery of particles of agent 102, and/or delivery of agent 102 using less fluid. Fluidization may break up agglomerates of agent 102. Agent 102 may include, for example, semi-cohesive materials, such as chitosan acetate.

Figure 7A:
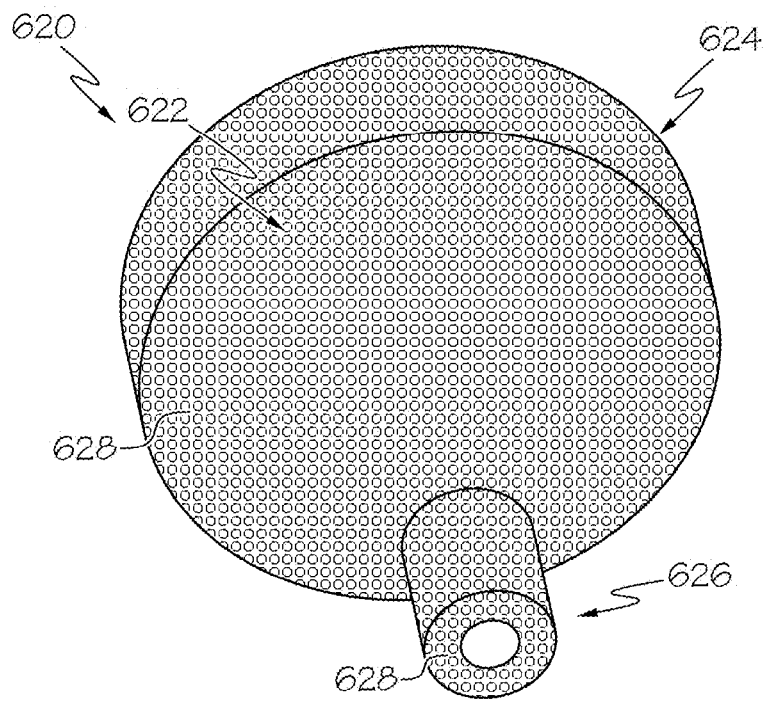
FIGS. 7A-8D depict exemplary filters for use with the enclosures of FIGS. 2A-5.

In one embodiment, as seen in FIG. 7A, a filter 620 may include an intermediate wall 622 disposed between a proximal portion 624 and a distal portion 626 of filter 620. A shape of filter 620 may be similar to the shape of filters 120, 220, 320, 420 described above. Proximal portion 624 may have a greater cross-sectional dimension than distal portion 626. Intermediate wall 622 may taper inwardly toward a distal direction relative to proximal portion 624, such that intermediate wall 622 may have a smaller cross-sectional dimension at an end adjacent to distal portion 626 than an opposing end adjacent to proximal portion 624. Stated differently, wall 622 may define a tapered surface and/or portion of filter 620, and may have a substantially funnel or conical shape, similar to filters 120, 220, 320, 420 shown and described above.

An inner surface of wall 622 may define a channel, which may receive agent 102. An angle between the inner surface of wall 622 may be greater than an angle of repose of agent 102 (e.g., the angle may be steeper than the angle of repose). Accordingly, agent 102 may flow freely along wall 622 due to a force of gravity. An inner surface of distal portion 626 may extend along a plane that is substantially parallel to a longitudinal axis of filter 620. Distal portion 626 may have a tubular shape, with substantially constant inner and outer diameters. Distal portion 626 may further include an opening at a distal end of distal portion 626, with the opening having a substantially similar diameter as that of the inner diameter of distal portion 626. The opening is in fluid communication with the channel of filter 620.

Filter 620 may be sintered (made via a sintering process) with a plurality of pores 628 formed through and within wall 622, proximal portion 624, and distal portion 626. The plurality of pores 628 may be formed about an entire perimeter of, and within all of, wall 622, proximal portion 624, and distal portion 626. In an embodiment, a size, shape, and/or distribution of the plurality of pores 628 may be substantially uniform relative to one another. In other embodiments, the plurality of pores 628 may have varying sizes, shapes, and/or spatial distribution relative to one another along and/or within one or more of wall 622, proximal portion 624, and/or distal portion 626. In some embodiments, filter 620 may be sintered, formed of a porous metal, formed of a lattice printed material, and more. By providing a sintered and/or porous filter, it should be appreciated that a fluidization consistency may be increased, and potential clogging caused by agent 102 may be reduced.

Figure 7B:
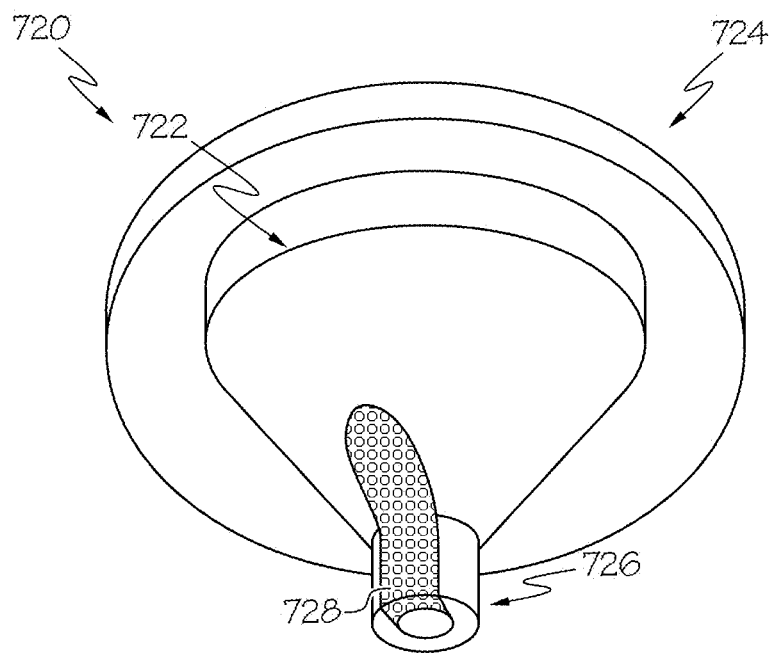
Figure 8A:
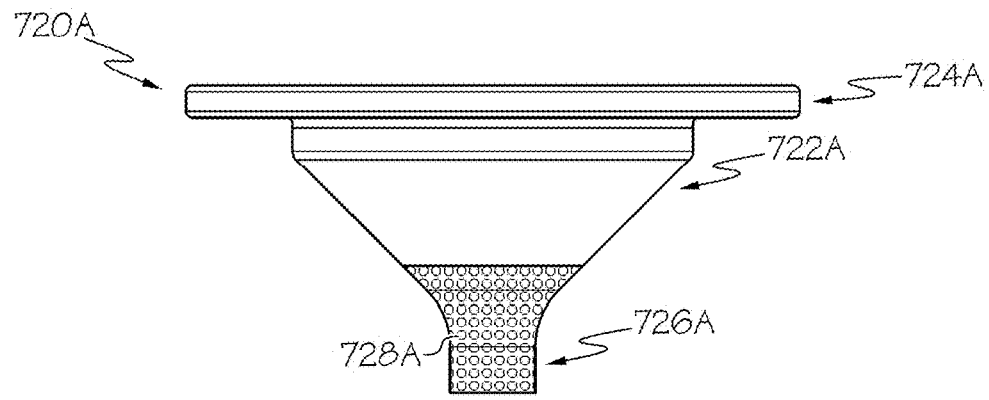
Figure 8B:
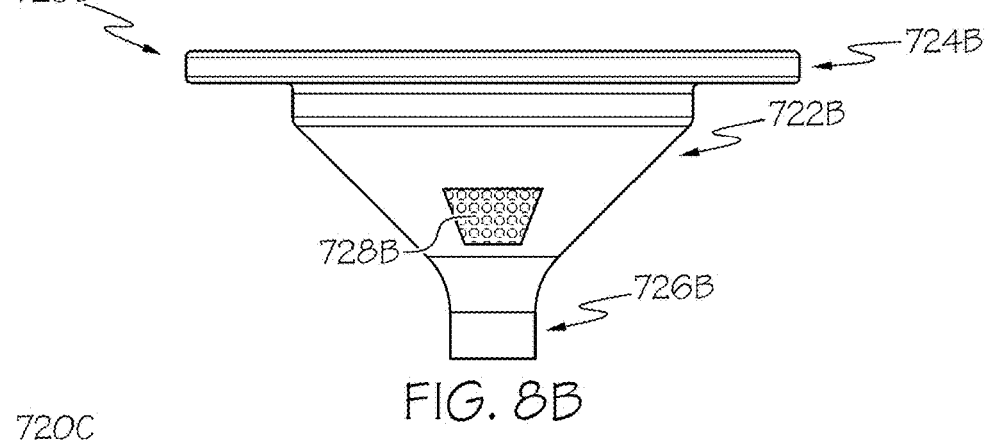
Figure 8C:
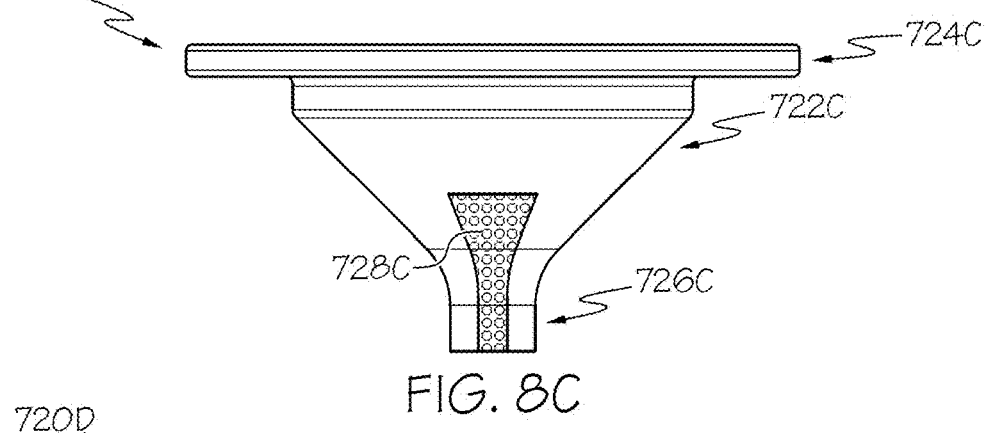
Figure 8D:
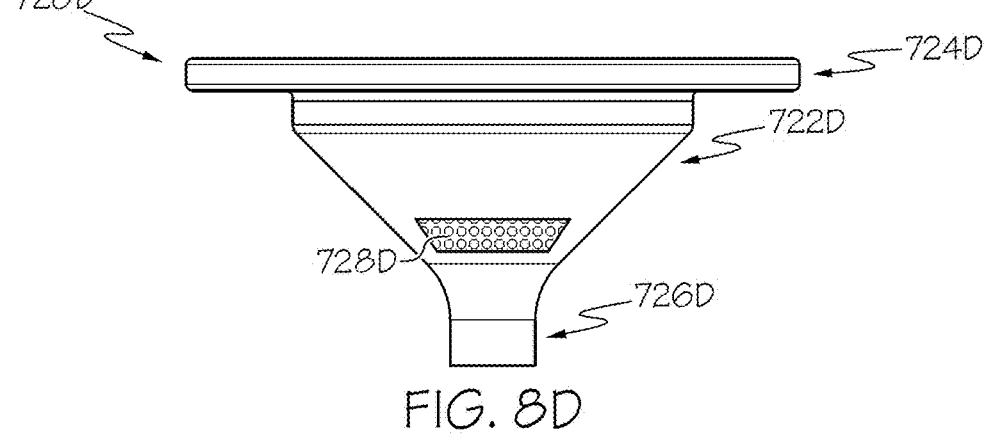

In further embodiments, as seen in FIG. 7B, a filter 720 may include a wall 722 disposed between a proximal portion 724 and a distal portion 726 with a plurality of pores 728 formed along and within at least a portion of wall 722 and distal portion 726. In the embodiment, a porous portion of filter 720 defined by the plurality of pores 728 may be formed through wall 722 along an end adjacent to distal portion 726, such as, for example, along a side surface of wall 722. It should be appreciated that a size, shape, and/or location of the porous portion and its plurality of pores 728 may determine a delivery rate of agent 102 from filter 720. In the embodiment of FIG. 7B, all portions of filter 720, other than the porous portion of pores 728, is solid, without pores, so that gas, fluid, or agent is unable to pass through. As shown and described in further detail herein, a size, location, and/or shape of the porous portion may provide varying fluidization performance capabilities for the filter, such as an average delivery rate of an agent from the filter.

As seen in FIGS. 8A-8D, the porous portion comprising a plurality of pores may be positioned along and/or within various sides and/or portions of the filter. Further, the porous portion may have various suitable sizes, shapes, heights, surface areas, and/or dimensions relative to the one or more sides and/or other portions of the filter. It should be appreciated that the filters shown in FIGS. 8A-8D are substantially similar to filter 720, such that substantially similar reference numerals are used to identify like components. The examples shown and described below were tested in simulated agent delivery conditions to compare the performance of the various designs. Other than the differences in sizes, shapes, and positions of the porous portions of the exemplary filters, environmental parameters influencing the operation and/or performance of the various exemplary filters were controlled when determining an average, minimum, and/or maximum agent delivery rate of each filter. For example, in determining the average, maximum, and minimum delivery rates described in detail below for each of the exemplary filters, one or more of a gas delivery rate (e.g., at 5 SLPM), a geometry of the filters, a particulate size of the powdered agent, and/or a type of the powdered agent were controlled across each of the exemplary filters.

For example, FIG. 8A shows a filter 720A having a porous portion defined by a plurality of pores 728A extending along and/or within a portion of wall 722A and a distal portion 728A of filter 720A. For example, the plurality of pores 728A may be extend about half a circumference of wall 722A and distal portion 726A. Stated differently, pores 728A may be formed about 180 degrees of an outer circumference of wall 722A and distal portion 726A. In the example, the plurality of pores 728A may be positioned along and/or within at least a portion of wall 722A and distal portion 726A, and pores 728A may define an internal surface area ranging from about 0.04770 $in^2$ (inches squared) to 0.04780 $in^2$, such as 0.04775 $in^2$. Pores 728A may have a height (longitudinal length) defined from a distal end of distal portion 726A ranging from about 0.30 in (inches) to 0.35 in, such as 0.32 in. The portion of wall 722A and distal portion 726A including pores 728A may be sized and/or shaped to control an average delivery rate of agent 102 at about 0.655 g/s, with a minimum delivery rate of about 0.556 g/s, a maximum delivery rate of about 0.692 g/s, and a standard deviation of about 0.066. It should be understood that the remaining portions and/or sides of filter 720A that exclude the porous portion may be formed of a solid (e.g., impermeable) surface devoid of any pores. Accordingly, agent 102 and/or a pressurized gas may be inhibited from flowing through the remaining portions and/or sides of filter 720A that have a solid configuration.

FIG. 8B shows another filter 720B having a porous portion defined by a plurality of pores 728B extending along and within a portion of only an intermediate wall 722B of filter 720B (only within the conical portion of filter 720). For example, pores 728B may extend about one-eighth of a circumference of wall 722B. Stated differently, pores 728B may be formed about 45 degrees of an outer circumference of wall 722B. In the example, the plurality of pores 728B may be positioned along and within at least one side of wall 722B, and pores 728B may define an internal surface area ranging from about 0.0234 $in^2$ to 0.02444 $in^2$, such as 0.0239 $in^2$. Pores 728B may have a height (longitudinal length) defined from a distal (bottom) end of the porous portion ranging from about 0.135 in (inches) to 0.145 in, such as 0.140 in. The portion of wall 722B including pores 728B may be sized and/or shaped to control an average delivery rate of agent 102 at about 0.935 g/s, with a minimum delivery rate of about 0.850 g/s, a maximum delivery rate of about 1.06 g/s, and a standard deviation of about 0.065. It should be understood that the remaining portions and/or sides of filter 720B that exclude the porous portion may be formed of a solid (e.g., impermeable) surface devoid of any pores. Accordingly, agent 102 and/or a pressurized gas may be inhibited from flowing through the remaining portions and/or sides of filter 720B that have a solid configuration.

FIG. 8C shows another filter 720C having a porous portion defined by a plurality of pores 728C extending along and within a portion of an intermediate wall 722C and a distal portion 726C of filter 720C. For example, pores 728C may extend about a quarter of a circumference of wall 722C and distal portion 726C. Stated differently, pores 728C may be formed about 90 degrees of an outer circumference of wall 722C and distal portion 726C. In the example, the plurality of pores 728C may be positioned along and within at least one side of wall 722C and distal portion 726C, and pores 728C may define an internal surface area ranging from about 0.0234 $in^2$ (inches squared) to 0.02444 $in^2$, such as 0.0239 $in^2$. Pores 728C may have a height (longitudinal length) defined from a distal end of distal portion 726C ranging from about 0.30 in (inches) to 0.35 in, such as 0.32 in. The portion of wall 722C and distal portion 726C including pores 728C may be sized and/or shaped to control an average delivery rate of agent 102 at about 0.374 g/s, with a minimum delivery rate of about 0.313 g/s, a maximum delivery rate of about 0.433 g/s, and a standard deviation of about 0.049.

In another example, pores 728C may extend about one-eighth of a circumference of wall 722C and distal portion 726C. Stated differently, pores 728C may be formed about 45 degrees of the outer circumference of wall 722C and distal portion 726C. Pores 728C may define an internal surface area ranging from about 0.0234 $in^2$ (inches squared) to 0.02444 $in^2$, such as 0.0239 $in^2$. Pores 728C may have a height (longitudinal length) defined from a distal end of distal portion 726C ranging from about 0.386 in (inches) to 0.396 in, such as 0.391 in. The portion of wall 722C and distal portion 726C including pores 728C may be sized and/or shaped to control an average delivery rate of agent 102 at about 0.733 g/s, with a minimum delivery rate of about 0.708 g/s, a maximum delivery rate of about 0.764 g/s, and a standard deviation of about 0.023.

In a further example, pores 728C may define an internal surface area ranging from about 0.0124 $in^2$ (inches squared) to 0.0115 $in^2$, such as 0.0119 $in^2$. Pores 728C may have a height (longitudinal length) defined from a distal end of distal portion 726C ranging from about 0.315 in (inches) to 0.325 in, such as 0.320 in. The portion of wall 722C and distal portion 726C with the plurality of pores 728C may be sized and/or shaped to control an average delivery rate of agent 102 at about 0.452 g/s, with a minimum delivery rate of about 0.385 g/s, a maximum delivery rate of about 0.550 g/s, and a standard deviation of about 0.059.

It should be understood that the remaining portions and/or sides of filter 720C that exclude the porous portion may be formed of a solid (e.g., impermeable) surface devoid of any pores. Accordingly, agent 102 and/or a pressurized gas may be inhibited from flowing through the remaining portions and/or sides of filter 720C that have a solid configuration.

FIG. 8D shows another filter 720D having a porous portion defined by a plurality of pores 728D extending along and within a portion of only an intermediate wall 722D (only within the conical portion) of filter 720D. For example, pores 728D may extend about a quarter of a circumference of wall 722D. Stated differently, pores 728D may be formed about 90 degrees of an outer circumference of wall 722D. In the example, the plurality of pores 728D may be positioned along and within at least one side of wall 722D, and pores 728D may define an internal surface area ranging from about 0.0234 $in^2$ to 0.02444 $in^2$, such as 0.0239 $in^2$. Pores 728D may have a height (longitudinal length) defined from a distal end of distal portion 726D ranging from about 0.080 in (inches) to 0.090 in, such as 0.085 in. The portion of wall 722D including pores 728D may be sized and/or shaped to control an average delivery rate of agent 102 at about 0.895 g/s, with a minimum delivery rate of about 0.726 g/s, a maximum delivery rate of about 1.05 g/s, and a standard deviation of about 0.131. It should be understood that the remaining portions and/or sides of filter 720D that exclude the porous portion may be formed of a solid (e.g., impermeable) surface devoid of any pores. Accordingly, agent 102 and/or a pressurized gas may be inhibited from flowing through the remaining portions and/or sides of filter 720D that have a solid configuration.

In some embodiments, a filter may include multiple discrete porous portions, including any combination of the porous portions shown and described in FIGS. 7B-8D. For example, an annular array of porous portions may be evenly or unevenly spaced about the circumference of the walls of a filter.

As seen in FIGS. 8A-8D, a size (e.g., height, surface area, circumference, etc.), shape, and position of the porous portion of the filter may determine a delivery rate of agent 102. It should be understood that the delivery rate of agent through the filter may be proportionate to or otherwise correlated with the size, shape, and/or position of the porous portion. Accordingly, the filter may be configured to deliver the agent 102 at higher delivery rates when the porous portion has a greater size and/or shape, for example. Further, the delivery rate of the filter may be increased when the porous portion is positioned along and/or within at least the intermediate wall (the conical portion), as compared to the distal portion. All else equal, having a greater amount of the porous portion in the intermediate wall increases a delivery rate of agent.

Agent 102 may include particles that have various shapes, including shard shapes, or substantially spherical (bead) shapes. Both shard and bead (substantially spherical) shaped particles may be fluidized, at a range of densities of the particles, as described below. The data described below may result from a fluid flow of 10 standard liters per minute (SLPM).

In one example, a semi-cohesive agent 102 may have a particle density of approximately 1.5 grams per cubic centimeter. Where the semi-cohesive particles are shard-shaped or substantially spherical and range in size from approximately 50 microns to approximately 425 microns, with an exit orifice size of 0.080 inches, a delivery rate may be approximately 1.80 grams per second. Where the semi-cohesive particles are shard-shaped or substantially spherical and range in size from approximately 355 microns to approximately 425 microns, with an exit orifice size of approximately 0.050 inches, a delivery rate may be approximately 0.3 grams per second to approximately 0.5 grams per second. Alternatively, shard-shaped particles with a size of approximately 500 microns-600 microns may be used with an exit orifice size of approximately 0.080 inches.

In another example, an agent 102 with a glass bead type of particle may have a particle density of approximately 2.7 grams per cubic centimeter and a substantially spherical shape. Where the particles have a size between approximately 500 microns and approximately 600 microns, and where an exit orifice has a size of approximately 0.080 inches, a delivery rate may be approximately 0.60 grams per second. Where the particles have a size between approximately 400 microns and approximately 450 microns, and where an exit orifice has a size of approximately 0.050 inches, a delivery rate may be approximately 0.38 grams per second. Where the particles have a size between approximately 400 microns and approximately 450 microns, and where an exit orifice has a size of approximately 0.080 inches, a delivery rate may be approximately 0.4 grams per second. Combinations of the particle sizes and delivery rates above may be used. For example, an orifice size of approximately 0.080 inches may be used with particle sizes between approximately 500 and approximately 600 microns, or between approximately 400 and approximately 450 microns, to achieve flow rates of approximately 0.38 grams per second, approximately 0.4 grams per second, or approximately 0.60 grams per second. In other examples, an orifice size of approximately 0.050 inches may be used with particle sizes between approximately 500 and approximately 600 microns, or between approximately 400 and approximately 450 microns, to achieve flow rates of approximately 0.38 grams per second, approximately 0.4 grams per second, or approximately 0.60 grams per second.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A device for delivering an agent, comprising:

a housing defining an enclosure, wherein the housing is configured to store an agent;

an inlet, in fluid communication with the enclosure, for receiving a flow of pressurized fluid;

an outlet in fluid communication with the enclosure;

a filter disposed within the enclosure, wherein a wall of the filter includes a plurality of pores, wherein the pores are configured such that the fluid is permitted to pass through the pores into a channel defined by an inner surface of the wall; and an actuation member disposed within the enclosure, wherein the actuation member is configured to transition between a first configuration, in which portions of the agent disposed proximally to the actuation member are prevented from passing distally of the actuation member, and a second configuration, in which portions of the agent disposed proximally of the actuation member are capable of passing distally of the actuation member;

wherein the actuation member includes a rotatable shaft, wherein the rotatable shaft includes an opening extending through the rotatable shaft substantially perpendicularly to a longitudinal axis of the rotatable shaft;

wherein in the first configuration, the actuation member is positioned relative to the enclosure with the opening not in fluid communication with the enclosure, such that the agent cannot enter the opening from the enclosure;

wherein in the second configuration, the actuation member is positioned relative to the enclosure with the opening in fluid communication with the enclosure, such that the agent is capable of passing through the opening from the enclosure to enter the outlet.

2. The device of claim 1, wherein the opening includes a first portion, in which a diameter of the opening tapers radially inward, in a distal direction, relative to a longitudinal axis of the opening, and a second portion, in which the diameter of the opening is constant.

3. The device of claim 2, wherein the opening includes a third portion, distal to the second portion, in which the diameter of the opening tapers radially outward, in a distal direction, relative to the longitudinal axis of the opening.

4. The device of claim 3, wherein the channel includes a first portion, in which a diameter of the channel tapers radially inward, in a distal direction, relative to a longitudinal axis of the channel.

5. The device of claim 4, wherein the first portion of the channel terminates distally in a distal end, and wherein the channel includes a second portion, adjacent to the distal end, in which the diameter of the channel is constant, wherein the second portion of the channel is proximal of the first portion of the opening.

6. The device of claim 5, wherein the channel includes a third portion, distal to the opening, wherein, in the third portion of the channel, the diameter of the channel tapers radially inward, in the distal direction, relative to the longitudinal axis of the channel.

7. The device of claim 1, wherein the filter is sintered, includes a porous metal, or includes a lattice printed material.

8. The device of claim 1, wherein the pores are configured such that the agent is not permitted to pass through the pores.

9. The device of claim 8, wherein the agent is a powder having a particle diameter between 50 microns and 600 microns, and wherein the pores have a diameter between 2 microns and 100 microns.

10. The device of claim 1, wherein the fluid is permitted to pass through the outlet in both the first configuration and the second configuration.

11. The device of claim 1, wherein the fluid exits the filter in a turbulent flow pattern.

12. The device of claim 1, wherein the rotatable shaft extends through one or more openings defined through one or more sides of the housing, and wherein the pores extend along tortuous paths.

13. The device of claim 12, wherein the one or more openings are defined by outwardly extending protrusions, wherein the protrusions extend outwardly relative to the housing.

14. The device of claim 1, wherein the rotatable shaft extends through the filter, wherein the rotatable shaft includes a first end and a second end, wherein the first end and the second end of the rotatable shaft each include a groove, wherein the groove of the first end and the groove of the second end each include a seal.

15. A device for delivering an agent, comprising:
a housing defining an enclosure, wherein the housing is configured to store an agent;
an inlet, in fluid communication with the enclosure, for receiving a flow of pressurized fluid;
a filter disposed within the enclosure, wherein a wall of the filter includes a plurality of pores, wherein the pores are configured such that the flow of fluid is permitted to pass through the pores into a channel defined by an inner surface of the wall, and wherein the pores are configured such that the agent is not permitted to pass through the pores;
an outlet in fluid communication with the channel;

an actuation member disposed within the enclosure, wherein the actuation member is configured to transition between a first configuration and a second configuration, in which the agent is not permitted to pass through the outlet when the actuation member is in the first configuration, and in which the agent is permitted to pass through the outlet when the actuation member is in the second configuration;
wherein the actuation member includes a rotatable shaft having an opening, wherein a longitudinal axis of the rotatable shaft is transverse to a longitudinal axis of the enclosure;
wherein in the first configuration, the actuation member is positioned relative to the enclosure with the opening not in fluid communication with the enclosure, such that the actuation member is configured to prevent the agent from entering the opening from the enclosure;
wherein in the second configuration, the actuation member is positioned relative to the enclosure with the opening in fluid communication with the enclosure, such that the actuation member is configured to allow the agent to pass through the opening from the enclosure to enter the outlet;
wherein the fluid is permitted to pass through the outlet in both the first configuration and the second configuration.

16. The device of claim 15, wherein fluid from the fluid inlet is only permitted to pass through the outlet after passing through the pores.

17. The device of claim 15, wherein the opening extends substantially perpendicularly to a longitudinal axis of the rotatable shaft.

18. A device for delivering an agent, comprising:
a housing defining an enclosure and configured to hold a powder, wherein the powder has a particle dimension between 50 microns and 600 microns;
an inlet in fluid communication with the enclosure for receiving a flow of pressurized gas;
a sintered filter disposed within the enclosure, wherein a wall of the filter includes a plurality of pores, wherein the pores are configured such that the gas is permitted to pass through the pores into a channel defined by a surface of the wall, and wherein the pores are configured such that the powder is not permitted to pass through the pores, wherein the pores have a diameter between 2 microns and 100 microns;
an actuation member that includes a rotatable shaft having an opening extending through the rotatable shaft substantially perpendicularly to a longitudinal axis of the rotatable shaft, and wherein, in a first configuration of the rotatable shaft, the agent is not permitted to pass through the opening, and wherein, in a second configuration of the rotatable shaft, the agent is permitted to pass through the opening; and
an outlet in fluid communication with the channel.

19. The medical device of claim 18, wherein the pores extend along tortuous paths.

* * * * *